United States Patent
Furusato et al.

(10) Patent No.: US 9,714,210 B2
(45) Date of Patent: *Jul. 25, 2017

(54) LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Yoshimasa Furusato, Chiba (JP); Masayuki Saito, Chiba (JP)

(73) Assignees: JNC CORPORATION, Tokyo (JP); JNC PETROCHEMICAL CORPORATION, Tokyo (JP)

(*) Notice: Subject to any disclaimer, the term of this patent is extended or adjusted under 35 U.S.C. 154(b) by 10 days.

This patent is subject to a terminal disclaimer.

(21) Appl. No.: 14/889,440

(22) PCT Filed: Apr. 17, 2014

(86) PCT No.: PCT/JP2014/060904
§ 371 (c)(1),
(2) Date: Nov. 6, 2015

(87) PCT Pub. No.: WO2014/192454
PCT Pub. Date: Dec. 4, 2014

(65) Prior Publication Data
US 2016/0083330 A1  Mar. 24, 2016

(30) Foreign Application Priority Data
May 28, 2013 (JP) .................... 2013-112259

(51) Int. Cl.
| | |
|---|---|
| *G02F 1/1333* | (2006.01) |
| *C07C 69/54* | (2006.01) |
| *C08F 20/30* | (2006.01) |
| *C09K 19/12* | (2006.01) |
| *C09K 19/30* | (2006.01) |
| *C09K 19/44* | (2006.01) |
| *C09K 19/54* | (2006.01) |
| *C09K 19/04* | (2006.01) |
| *C09K 19/34* | (2006.01) |

(52) U.S. Cl.
CPC .............. *C07C 69/54* (2013.01); *C08F 20/30* (2013.01); *C09K 19/12* (2013.01); *C09K 19/3066* (2013.01); *C09K 19/3068* (2013.01); *C09K 19/3402* (2013.01); *C09K 19/44* (2013.01); *C09K 19/542* (2013.01); *C09K 2019/0444* (2013.01); *C09K 2019/0448* (2013.01); *C09K 2019/122* (2013.01); *C09K 2019/123* (2013.01); *C09K 2019/301* (2013.01); *C09K 2019/3021* (2013.01); *C09K 2019/3025* (2013.01); *C09K 2019/3027* (2013.01); *C09K 2019/3078* (2013.01); *C09K 2019/3422* (2013.01); *C09K 2019/3425* (2013.01)

(58) Field of Classification Search
CPC .... C09K 19/3068; C09K 19/12; C09K 19/44; C09K 19/3066; C09K 19/3402; C09K 19/542; C09K 2019/0444; C09K 2019/0448; C09K 2019/122; C09K 2019/123; C09K 2019/301; C09K 2019/3021; C09K 2019/3025; C09K 2019/3027; C09K 2019/3078; C09K 2019/3422; C09K 2019/3425; C07C 69/54; C08F 20/30
USPC ................. 252/299.01, 299.6; 349/182, 183
See application file for complete search history.

(56) References Cited

U.S. PATENT DOCUMENTS

| | | | |
|---|---|---|---|
| 9,090,822 B2* | 7/2015 | Goetz ................ | C09K 19/12 |
| 2012/0224124 A1 | 9/2012 | Goetz et al. | |
| 2014/0346399 A1 | 11/2014 | Fujita et al. | |
| 2016/0075950 A1* | 3/2016 | Kobayashi .......... | C08F 20/26 |
| | | | 252/299.01 |

FOREIGN PATENT DOCUMENTS

| | | |
|---|---|---|
| JP | 2012-018215 | 1/2012 |
| JP | 2013-509457 | 3/2013 |
| WO | 2013054682 | 3/2015 |

OTHER PUBLICATIONS

"International Search Report (Form PCT/ISA/210)", mailed on Jul. 22, 2014, with English translation thereof, pp. 1-4, in which two of the listed references (WO2013054682 and JP2013-509457) were cited.

* cited by examiner

*Primary Examiner* — Geraldina Visconti
(74) *Attorney, Agent, or Firm* — Jianq Chyun IP Office

(57) ABSTRACT

A liquid crystal composition satisfies at least one of characteristics such as a high maximum temperature, a low minimum temperature, small viscosity, suitable optical anisotropy, large negative dielectric anisotropy, large specific resistance, high stability to ultraviolet light, to heat or the like, or has a suitable balance regarding at least two of the characteristics; and an AM device has characteristics such as a short response time, a large voltage holding ratio, a low threshold voltage, a large contrast ratio and a long service life. The liquid crystal composition contains a specific compound having at least two polymerizable groups, and the liquid crystal display device includes the composition. The composition contains a specific compound having large negative dielectric anisotropy as a first component, and may contain a specific compound having the high maximum temperature or the small viscosity as a second component.

17 Claims, No Drawings

LIQUID CRYSTAL COMPOSITION AND LIQUID CRYSTAL DISPLAY DEVICE

CROSS-REFERENCE TO RELATED APPLICATION

This application is a 371 application of International PCT application serial no. PCT/JP2014/060904, filed on Apr. 17, 2014, which claims the priority benefit of Japan application no. 2013-112259, filed on May 28, 2013. The entirety of each of the above-mentioned patent applications is hereby incorporated by reference herein and made a part of this specification.

TECHNICAL FIELD

The invention relates to a liquid crystal composition, a liquid crystal display device including the composition and so forth. In particular, the invention relates to a liquid crystal composition having a negative dielectric anisotropy, and a liquid crystal display device that includes the liquid crystal composition and has a mode such as an IPS mode, a VA mode, an FFS mode and an FPA mode. The invention also relates to a liquid crystal display device having a polymer sustained alignment mode.

BACKGROUND ART

In a liquid crystal display device, a classification based on an operating mode for liquid crystals includes a phase change (PC) mode, a twisted nematic (TN) mode, a super twisted nematic (STN) mode, an electrically controlled birefringence (ECB) mode, an optically compensated bend (OCB) mode, an in-plane switching (IPS) mode, a vertical alignment (VA) mode, a fringe field switching (FFS) or a field induced photo-reactive alignment (FPA) mode. A classification based on a driving mode in the device includes a passive matrix (PM) and an active matrix (AM). The PM is classified into static and multiplex and so forth. The AM is classified into a thin film transistor (TFT), a metal insulator metal (MIM) and so forth. The TFT is further classified into amorphous silicon and polycrystal silicon. The latter is classified into a high temperature type and a low temperature type based on a production process. A classification based on a light source includes a reflection type utilizing natural light, a transmissive type utilizing backlight and a transflective type utilizing both the natural light and the backlight.

The liquid crystal display device includes a liquid crystal composition having a nematic phase. The composition has suitable characteristics. An AM device having good characteristics can be obtained by improving characteristics of the composition. Table 1 below summarizes a relationship of the characteristics between two aspects. The characteristics of the composition will be further described based on a commercially available AM device. A temperature range of the nematic phase relates to a temperature range in which the device can be used. A preferred maximum temperature of the nematic phase is about 70° C. or higher, and a preferred minimum temperature of the nematic phase is about −10° C. or lower. Viscosity of the liquid crystal composition relates to a response time of the device. A short response time is preferred for displaying moving images on the device. A shorter response time even by one millisecond is desirable. Accordingly, a small viscosity of the composition is preferred. A small viscosity at a low temperature is further preferred.

TABLE 1

Characteristics of Composition and AM Device

| No. | Characteristics of Composition | Characteristics of AM Device |
|---|---|---|
| 1 | Wide temperature range of a nematic phase | Wide usable temperature range |
| 2 | Small viscosity[1] | Short response time |
| 3 | Suitable optical anisotropy | Large contrast ratio |
| 4 | Large positive or negative dielectric anisotropy | Low threshold voltage and small electric power consumption Large contrast ratio |
| 5 | Large specific resistance | Large voltage holding ratio and large contrast ratio |
| 6 | High stability to ultraviolet light and heat | Long service life |

[1] A liquid crystal composition can be injected into a liquid crystal display device in a short time.

An optical anisotropy of the composition relates to a contrast ratio in the device. According to a mode of the device, a large optical anisotropy or a small optical anisotropy, more specifically, a suitable optical anisotropy is required. A product (Δn×d) of the optical anisotropy (Δn) of the composition and a cell gap (d) in the device is designed so as to maximize the contrast ratio. A suitable value of the product depends on a type of the operating mode. The suitable value is in the range of about 0.30 micrometer to about 0.40 micrometer in a device having the VA mode, and is in the range of about 0.20 micrometer to about 0.30 micrometer in a device having the IPS mode or the FFS mode. In the above cases, a composition having the large optical anisotropy is preferred for a device having a small cell gap. A large dielectric anisotropy in the composition contributes to a low threshold voltage, a small electric power consumption and a large contrast ratio in the device. Accordingly, the large dielectric anisotropy is preferred. A large specific resistance in the composition contributes to a large voltage holding ratio and the large contrast ratio in the device. Accordingly, a composition having the large specific resistance at room temperature and also at a high temperature in an initial stage is preferred. The composition having the large specific resistance at room temperature and also at a high temperature after the device has been used for a long period of time is preferred. Stability of the composition to ultraviolet light and heat relates to a service life of the liquid crystal display device. In the case where the stability is high, the device has a long service life. Such characteristics are preferred for an AM device used in a liquid crystal projector, a liquid crystal television and so forth.

In a liquid crystal display device having a polymer sustained alignment (PSA) mode, a liquid crystal composition containing a polymer is used. First, a composition to which a small amount of the polymerizable compound is added is injected into the device. Then, the composition is irradiated with ultraviolet light while voltage is applied between substrates of the device. The polymerizable compound polymerizes to form a network structure of the polymer in the liquid crystal composition. In the composition, alignment of liquid crystal molecules can be controlled by the polymer, and therefore the response time of the device is shortened and also image persistence is improved. Such an effect of the polymer can be expected for a device having the mode such as the TN mode, the ECB mode, the OCB mode, the IPS mode, the VA mode, the FFS mode and the FPA mode.

A composition having a positive dielectric anisotropy is used for an AM device having the TN mode. In an AM device having the VA mode, a composition having a negative dielectric anisotropy is used. A composition having the positive or negative dielectric anisotropy is used for an AM device having the IPS mode, the FFS mode or the FPA mode. An example of a composition for a device having the polymer sustained alignment (PSA) mode is disclosed in patent literature No. 1.

CITATION LIST

Patent Literature

Patent literature No. 1: JP 2012-018215 A

SUMMARY OF THE INVENTION

Technical Problem

One of aims of the invention is to provide a liquid crystal composition satisfying at least one of characteristics such as a high maximum temperature of a nematic phase, a low minimum temperature of the nematic phase, a small viscosity, a suitable optical anisotropy, a large negative dielectric anisotropy, a large specific resistance, a high stability to ultraviolet light and a high stability to heat. Another aim is to provide a liquid crystal composition having a suitable balance regarding at least two of the characteristics. Another aim is to provide a liquid crystal display device including such a composition. Another aim is to provide an AM device having characteristics such as a short response time, a large voltage holding ratio, a low threshold voltage, a large contrast ratio and a long service life.

Solution to Problem

The invention concerns a liquid crystal composition that has a negative dielectric anisotropy and contains a polymerizable compound having at least two polymerizable groups in which at least one polymerizable group is acryloyloxy or methacryloyloxy, and at least one polymerizable group is a polymerizable group selected from the group of groups represented by formula (P-1), formula (P-2) or formula (P-3), and concerns a liquid crystal display device including the composition:

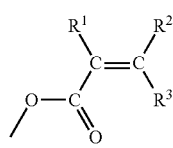

(P-1)

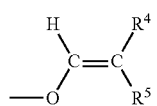

(P-2)

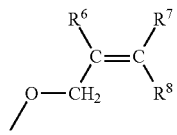

(P-3)

wherein, in formula (P-1) to formula (P-3), $R^1$, $R^2$, $R^3$, $R^4$, $R^5$, $R^6$, $R^7$ or $R^8$ is independently hydrogen, fluorine, alkyl having 1 to 5 carbons, or alkyl having 1 to 5 carbons in which at least one of hydrogen is replaced by halogen;

in formula (P-1), when $R^1$ is hydrogen or methyl, at least one of $R^2$ and $R^3$ is fluorine, alkyl having 1 to 5 carbons, or alkyl having 1 to 5 carbons in which at least one of hydrogen is replaced by halogen;

in formula (P-2), at least one of $R^4$ and $R^5$ is fluorine, alkyl having 1 to 5 carbons, or alkyl having 1 to 5 carbons in which at least one of hydrogen is replaced by halogen; and in formula (P-3), at least one of $R^6$, $R^7$ and $R^8$ is fluorine, alkyl having 1 to 5 carbons, or alkyl having 1 to 5 carbons in which at least one of hydrogen is replaced by halogen.

Advantageous Effects of Invention

An advantage of the invention is a liquid crystal composition satisfying at least one of characteristics such as a high maximum temperature of a nematic phase, a low minimum temperature of the nematic phase, a small viscosity, a large optical anisotropy, a large negative dielectric anisotropy, a large specific resistance, a high stability to ultraviolet light and a high stability to heat. Another advantage is a liquid crystal composition having a suitable balance regarding at least two of the characteristics. Another advantage is a liquid crystal display device including such a composition. Another advantage is an AM device having characteristics such as a short response time, a large voltage holding ratio, a low threshold voltage, a large contrast ratio and a long service life.

DESCRIPTION OF EMBODIMENTS

Usage of terms herein is as described below. Terms "liquid crystal composition" and "liquid crystal display device" may be occasionally abbreviated as "composition" and "device," respectively. The liquid crystal display device is a generic term for a liquid crystal display panel and a liquid crystal display module. A liquid crystal compound is a generic term for a compound having a liquid crystal phase such as a nematic phase and a smectic phase, and a compound having no liquid crystal phase but to be mixed with a composition for the purpose of adjusting characteristics such as a temperature range of the nematic phase, viscosity and a dielectric anisotropy. The compound has a six-membered ring such as 1,4-cyclohexylene and 1,4-phenylene, and rod like molecular structure. A polymerizable compound is added for the purpose of forming a polymer in the composition.

The liquid crystal composition is prepared by mixing a plurality of liquid crystal compounds. A ratio (content) of the liquid crystal compounds is expressed in terms of weight percent (% by weight) based on the weight of the liquid crystal composition. An additive such as an optically active compound, an antioxidant, an ultraviolet light absorber, a dye, an antifoaming agent, the polymerizable compound, a polymerization initiator and a polymerization inhibitor is added to the liquid crystal composition when necessary. A ratio (content) of the additive is expressed in terms of weight percent (% by weight) based on the weight of the liquid crystal composition in a manner similar to the ratio of the liquid crystal compound. Weight parts per million (ppm) may be occasionally used. A ratio of the polymerization initiator and the polymerization inhibitor is exceptionally expressed based on the weight of the polymerizable compound.

An expression "maximum temperature range of the nematic phase" may be occasionally abbreviated as "maximum temperature." An expression "minimum temperature range of the nematic phase" may be occasionally abbreviated as "minimum temperature." An expression "having a large specific resistance" means that the composition has a large specific resistance at room temperature and also at a temperature close to the maximum temperature of the nematic phase in an initial stage, and the composition has the large specific resistance at room temperature and also at a temperature close to the maximum temperature of the nematic phase even after the device has been used for a long period of time. An expression "having a large voltage holding ratio" means that the device has a large voltage holding ratio at room temperature and also at a temperature close to the maximum temperature of the nematic phase in the initial stage, and the device has the large voltage holding ratio at room temperature and also at a temperature close to the maximum temperature of the nematic phase even after the device has been used for the long period of time. An expression "increase the dielectric anisotropy" means that a value of dielectric anisotropy positively increases in a liquid crystal composition having a positive dielectric anisotropy, and the value of dielectric anisotropy negatively increases in a liquid crystal composition having a negative dielectric anisotropy.

An expression "at least one of 'A' may be replaced by 'B'" means that the number of 'A' is arbitrary. A position of 'A' is arbitrary when the number of 'A' is 1, and also positions thereof can be selected without restriction when the number of 'A' is 2 or more. A same rule also applies to an expression "at least one of 'A' is replaced by 'B'."

A symbol of terminal group $R^9$ is used for a plurality of compounds in chemical formulas of component compounds. In the compounds, two groups represented by two of arbitrary $R^9$ may be identical or different. In one case, for example, $R^9$ of compound (2-1) is ethyl and $R^9$ of compound (2-2) is ethyl. In another case, for example, $R^9$ of compound (2-1) is ethyl and $R^9$ of compound (2-2) is propyl. A same rule also applies to any other symbol of a terminal group or the like. In formula (2), when j is 2, two of ring D exist. In the compound, two rings represented by two of ring D may be identical or different. A same rule applies to two of arbitrary ring D when j is larger than 2. A same rule also applies to a symbol of the other ring and a bonding group or the like.

In compound (1) or the like, a hexagonal shape represents a ring that is not always a six-membered ring. An oblique line crossing the hexagonal shape means that arbitrary hydrogen on the ring may be replaced by a group such as $P^1$-$Sp^1$. A subscript such as b represents the number of groups subjected to replacement, and the case where b is 0 means that no replacement is made. A same rule also applies to $P^6$-$Sp^4$ or the like of compound (4).

Then, 2-fluoro-1,4-phenylene means two divalent groups described below. In the chemical formula, fluorine may be leftward (L) or rightward (R). A same rule also applies to a divalent group in an asymmetrical ring, such as tetrahydropyran-2,5-diyl.

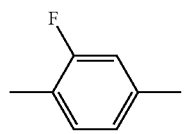

(L)

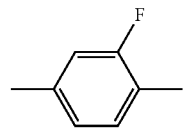

(R)

The invention includes the items described below.

Item 1. A liquid crystal composition that has a negative dielectric anisotropy, and contains a polymerizable compound having at least two polymerizable groups in which at least one polymerizable group is acryloyloxy or methacryloyloxy, and at least one polymerizable group is a polymerizable group selected from the group of groups represented by formula (P-1), formula (P-2) or formula (P-3):

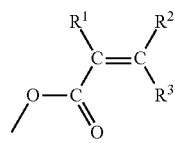

(P-1)

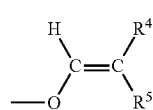

(P-2)

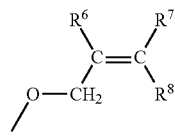

(P-3)

wherein, in formula (P-1) to formula (P-3), $R^1$, $R^2$, $R^3$, $R^4$, $R^5$, $R^6$, $R^7$ or $R^8$ is independently hydrogen, fluorine, alkyl having 1 to 5 carbons, or alkyl having 1 to 5 carbons in which at least one of hydrogen is replaced by halogen;

in formula (P-1), when $R^1$ is hydrogen or methyl, at least one of $R^2$ and $R^3$ is fluorine, alkyl having 1 to 5 carbons, or alkyl having 1 to 5 carbons in which at least one of hydrogen is replaced by halogen;

in formula (P-2), at least one of $R^4$ and $R^5$ is fluorine, alkyl having 1 to 5 carbons, or alkyl having 1 to 5 carbons in which at least one of hydrogen is replaced by halogen; and in formula (P-3), at least one of $R^6$, $R^7$ and $R^6$ is fluorine, alkyl having 1 to 5 carbons, or alkyl having 1 to 5 carbons in which at least one of hydrogen is replaced by halogen.

Item 2. The liquid crystal composition according to item 1, wherein the polymerizable compound has at least two polymerizable groups in which at least one polymerizable group is acryloyloxy or methacryloyloxy, and at least one polymerizable group is 2-butenoyloxy, 2-methyl-2-butenoyloxy, 2-methylenebutanoyloxy, 2-methyl-1-propenyloxy, 2,2-difluoro vinyloxy, 2-butenyloxy, 2-methyl-2-butenyloxy or 2-methyl-2-propenyloxy.

Item 3. The liquid crystal composition according to item 1 or 2, wherein the polymerizable compound is at least one compound selected from the group of compounds represented by formula (1):

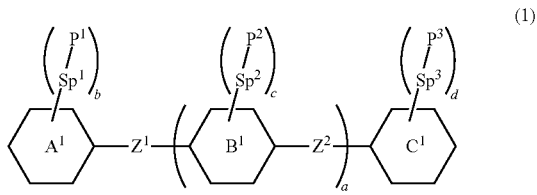

(1)

wherein, in formula (1), ring $A^1$ or ring $C^1$ is independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one of hydrogen may be replaced by halogen, alkyl having 1 to 12 carbons, or alkyl having 1 to 12 carbons in which at least one of hydrogen is replaced by halogen; ring $B^1$ is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one of hydrogen may be replaced by halogen, alkyl having 1 to 12 carbons, or alkyl having 1 to 12 carbons in which at least one of hydrogen may be replaced by halogen; $Z^1$ or $Z^2$ is independently a single bond or alkylene having 1 to 10 carbons, in the alkylene, at least one of —$CH_2$— may be replaced by —O—, —CO—, —COO— or —OCO—, at least one of —$CH_2$—$CH_2$— may be replaced by —CH═CH—, —C($CH_3$)═CH—, —CH═C($CH_3$)— or —C($CH_3$)═C($CH_3$)—, and in the groups, at least one of hydrogen may be replaced by fluorine or chlorine; at least one of $P^1$, $P^2$ and $P^3$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy, 2-methyl-2-butenyloxy or 2-methyl-2-propenyloxy; $Sp^1$, $Sp^2$ or $Sp^3$ is independently a single bond or alkylene having carbons 1-10, in the alkylene, at least one of —$CH_2$— may be replaced by —O—, —COO—, —OCO— or —OCOO—, at least one of —$CH_2$—$CH_2$— may be replaced by —CH═CH— or —C≡C—, and in the groups, at least one of hydrogen may be replaced by fluorine or chlorine; a is 0, 1 or 2; and b, c or d is independently an integer from 0 to 4, and a sum of b, c, and d is 2 or more.

Item 4. The liquid crystal composition according to any one of items 1 to 3, wherein the polymerizable compound is at least one compound selected from the group of compounds represented by formula (1-1):

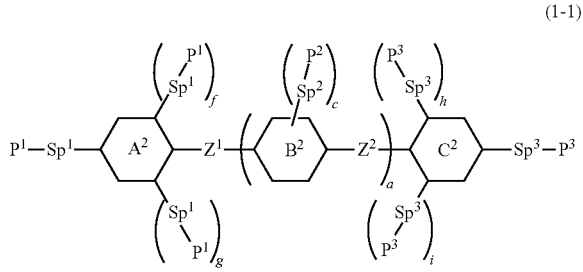

(1-1)

wherein, in formula (1-1), ring $A^2$, ring $B^2$ or ring $C^2$ is independently 1,4-cyclohexylene, 1,4-cyclohexenylene, 1,4-phenylene, naphthalene-1,2-diyl, naphthalene-1,4-diyl, naphthalene-1,5-diyl, naphthalene-1,7-diyl, naphthalene-1,8-diyl, naphthalene-2,3-diyl or naphthalene-2,6-diyl, and in the rings, at least one of hydrogen may be replaced by halogen, alkyl having 1 to 12 carbons, or alkyl having 1 to 12 carbons in which at least one of hydrogen is replaced by halogen; $Z^1$ or $Z^2$ is independently a single bond or alkylene having 1 to 10 carbons, in the alkylene, at least one of —$CH_2$— may be replaced by —O—, —CO—, —COO— or —OCO—, at least one of —$CH_2$—$CH_2$— may be replaced by —CH═CH—, —C($CH_3$)═CH—, —CH═C($CH_3$)— or —C($CH_3$)═C($CH_3$)—, and in the groups, at least one of hydrogen may be replaced by fluorine or chlorine; at least one of $P^1$, $P^2$ and $P^3$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy, 2-methyl-2-butenyloxy or 2-methyl-2-propenyloxy; $Sp^1$, $Sp^2$ or $Sp^3$ is independently a single bond or alkylene having 1 to 10 carbons, in the alkylene, at least one of —$CH_2$— may be replaced by —O—, —COO—, —OCO— or —OCOO—, at least one of —$CH_2$—$CH_2$— may be replaced by —CH═CH— or —C≡C—, and in the groups, at least one of hydrogen may be replaced by fluorine or chlorine; a is 0, 1 or 2; and c is an integer from 0 to 4, f, g, h and i each are 0 or 1, and a sum of c, f, g, h and i is 1 or more.

Item 5. The liquid crystal composition according to any one of items 1 to 4, wherein the polymerizable compound is at least one compound selected from the group of compounds represented by formula (1-1-1):

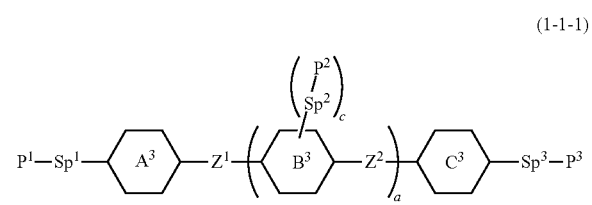

(1-1-1)

wherein, in formula (1-1-1), ring $A^3$, ring $B^3$ or ring $C^3$ is independently 1,4-phenylene in which at least one of hydrogen may be replaced by halogen, alkyl having 1 to 12 carbons, or alkyl having 1 to 12 carbons in which at least one of hydrogen is replaced by halogen; $Z^1$ or $Z^2$ is independently a single bond, —COO—, —CH═CH—, —CH═COO—, —C($CH_3$)═CH—COO—, —CH═O($CH_3$)—COO—, —C($CH_3$)═C($CH_3$)—COO—, —COCH═CH—, —C($CH_3$)═C($CH_3$)—, —CH═CH—$CH_2$O—, —CH═CH—O$CH_2$— or —CO—; at least one of $P^1$, $P^2$ and $P^3$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy, 2-methyl-2-butenyloxy, or 2-methyl-2-propenyloxy; $Sp^1$, $Sp^2$ or $Sp^3$ is independently a single bond or alkylene having 1 to 10 carbons, in the alkylene, at least one of —$CH_2$— may be replaced by —O—, —COO—, —OCO— or —OCOO—, at least one of —$CH_2$—$CH_2$— may be replaced by —CH═CH— or —C≡C—, and in the groups, at least one of hydrogen may be replaced by fluorine or chlorine; a is 0, 1 or 2; and c is an integer from 0 to 4.

Item 6. The liquid crystal composition according to any one of items 1 to 5, wherein the polymerizable compound is at least one compound selected from the group of compounds represented by formula (1-1-1-1) to formula (1-1-1-12):

(1-1-1-1)
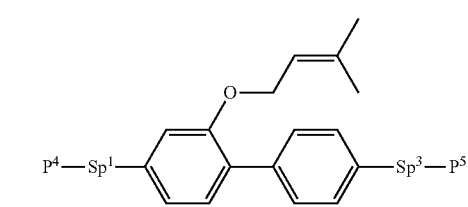
(1-1-1-2)
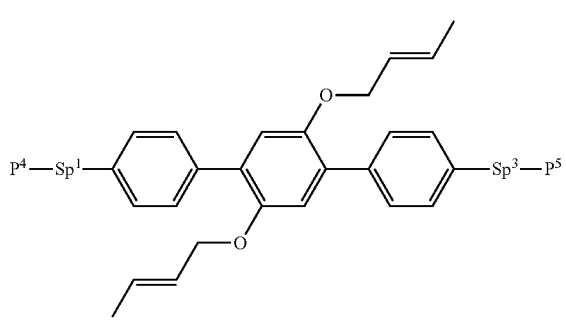
(1-1-1-3)
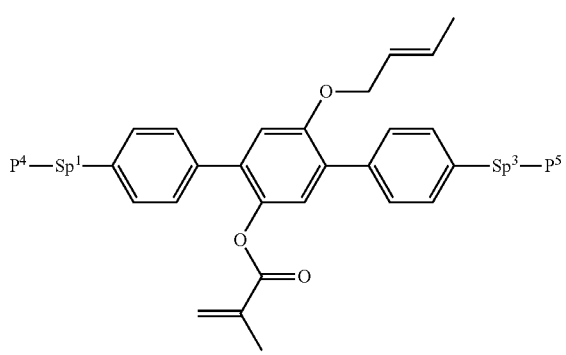
(1-1-1-4)
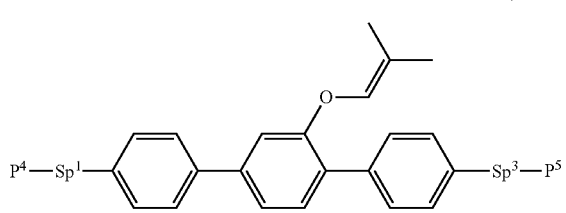
(1-1-1-5)
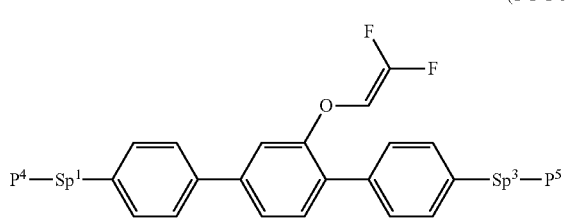
(1-1-1-6)
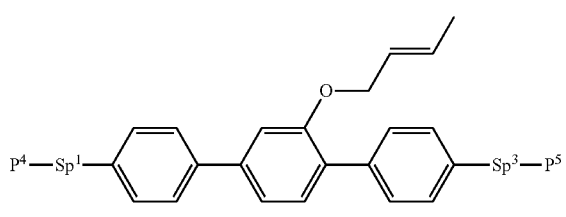
(1-1-1-7)
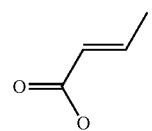
(1-1-1-8)
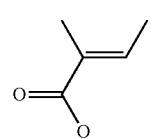
(1-1-1-9)
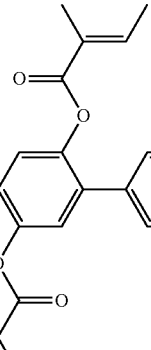
(1-1-1-10)
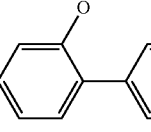
(1-1-1-11)
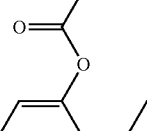

(1-1-1-12)

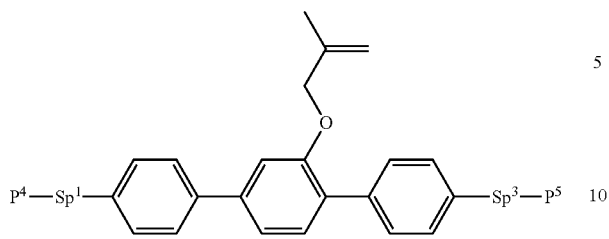

wherein, in formula (1-1-1-1) to formula (1-1-1-12), P⁴ or P⁵ is independently acryloyloxy or methacryloyloxy; Sp¹ or Sp³ is independently a single bond or alkylene having 1 to 10 carbons, in the alkylene, at least one of —CH₂— may be replaced by —O—, —COO—, —OCO— or —OCOO—, at least one of —CH₂—CH₂— may be replaced by —CH═CH— or —C≡C—, and in the groups, at least one of hydrogen may be replaced by fluorine or chlorine.

Item 7. The liquid crystal composition according to any one of items 1 to 6, containing at least one compound selected from the group of compounds represented by formula (2) as a first component:

(2)

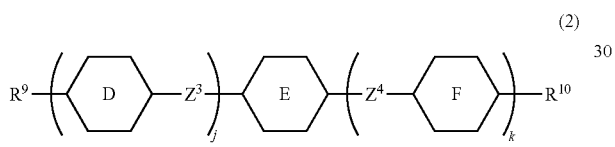

wherein, in formula (2), R⁹ or R¹⁰ is independently alkyl having 1 to 12 carbons, alkoxy having 1 to 12 carbons, alkenyl having 2 to 12 carbons or alkenyloxy having 2 to 12 carbons; ring D or ring F is independently 1,4-cyclohexylene, 1,4-phenylene, 1,4-phenylene in which at least one of hydrogen is replaced by fluorine or chlorine or tetrahydropyran-2,5-diyl; ring E is 2, 3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl; Z³ or Z⁴ is independently a single bond, —CH₂CH₂—, —CH₂O—, —OCH₂—, —COO— or —OCO—; j is 1, 2 or 3, k is 0 or 1, and a sum of j and k is 3 or less.

Item 8. The liquid crystal composition according to any one of items 1 to 7, containing at least one compound selected from the group of compounds represented by formula (2-1) to formula (2-19) as the first component:

(2-1)

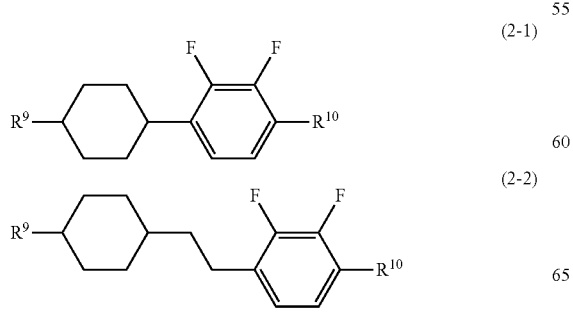

(2-2)

(2-3)

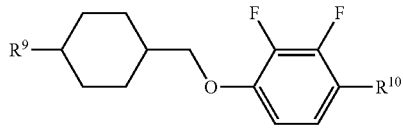

(2-4)

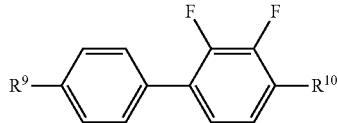

(2-5)

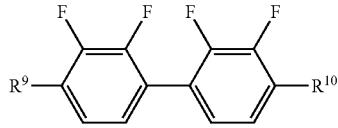

(2-6)

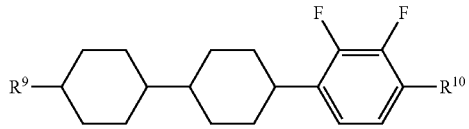

(2-7)

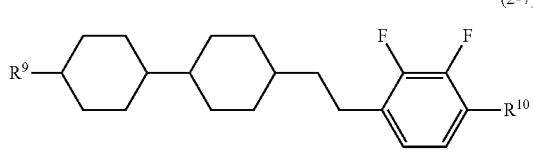

(2-8)

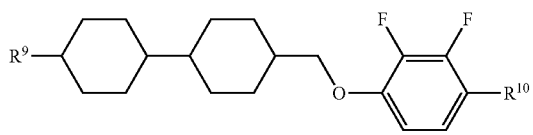

(2-9)

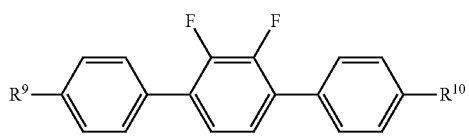

(2-10)

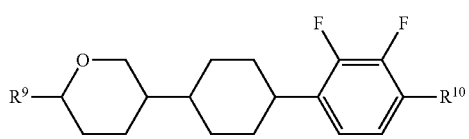

(2-11)

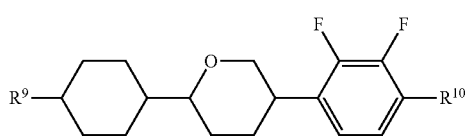

(2-12)

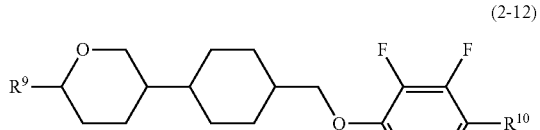

(2-13)

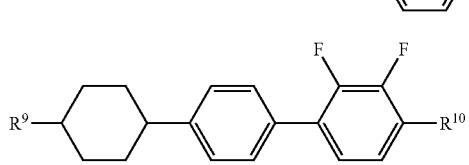

-continued (2-14)
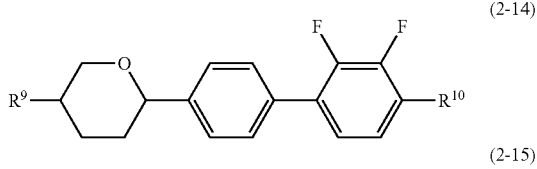

(2-15)
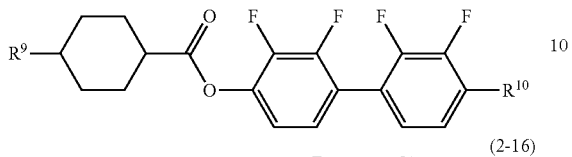

(2-16)
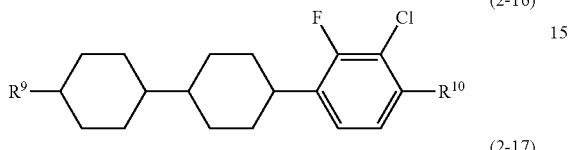

(2-17)
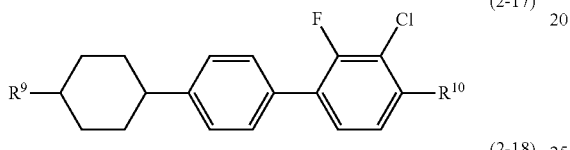

(2-18)
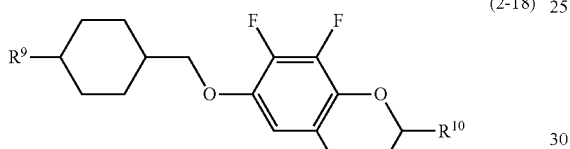

(2-19)
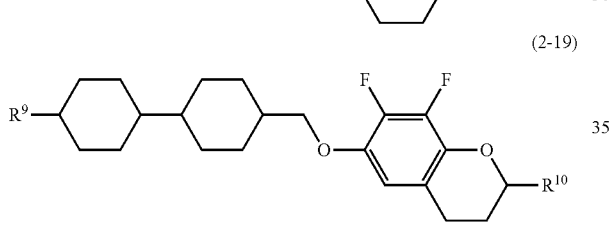

wherein, in formula (2-1) to formula (2-19), $R^9$ or $R^{10}$ is independently alkyl having 1 to 12 carbons, alkoxy having 1 to 12 carbons, alkenyl having 2 to 12 carbons or alkenyloxy having 2 to 12 carbons.

Item 9. The liquid crystal composition according to item 7 or 8, wherein a ratio of the first component is in the range of 10% by weight to 90% by weight based on the weight of the liquid crystal composition.

Item 10. The liquid crystal composition according to any one of items 1 to 9, containing at least one compound selected from the group of compounds represented by formula (3) as a second component:

(3)
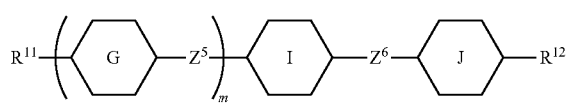

wherein, in formula (3), $R^{11}$ or $R^{12}$ is independently alkyl having 1 to 12 carbons, alkoxy having 1 to 12 carbons, alkenyl having 2 to 12 carbons, or alkenyl having 2 to 12 carbons in which at least one of hydrogen is replaced by fluorine; ring G, ring I or ring J is independently 1,4-cyclohexylene, 1,4-phenylene or 2-fluoro-1,4-phenylene; $Z^5$ or $Z^6$ is independently a single bond, —$CH_2CH_2$—, —$CH_2O$—, —$OCH_2$—, —COO— or —OCO—; and m is 0, 1 or 2.

Item 11. The liquid crystal composition according to any one of items 1 to 10, containing at least one compound selected from the group of compounds represented by formula (3-1) to formula (3-13) as the second component:

(3-1)
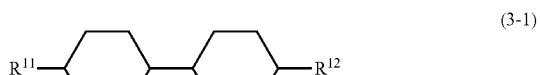

(3-2)
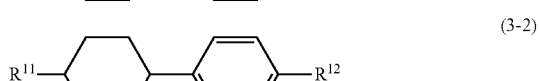

(3-3)
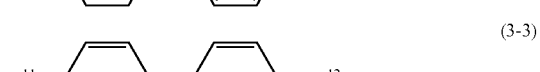

(3-4)
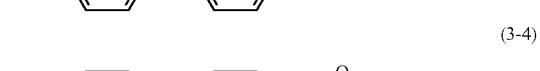

(3-5)
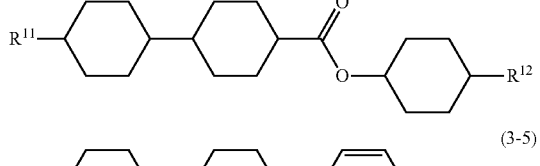

(3-6)
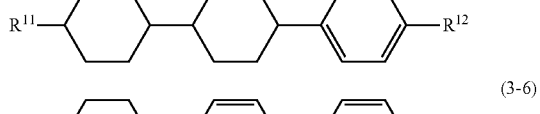

(3-7)
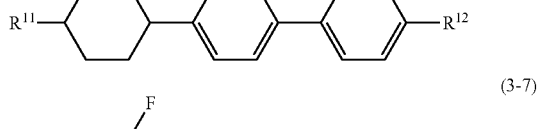

(3-8)
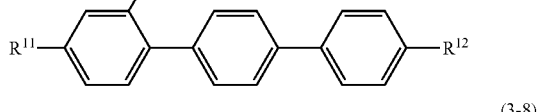

(3-9)
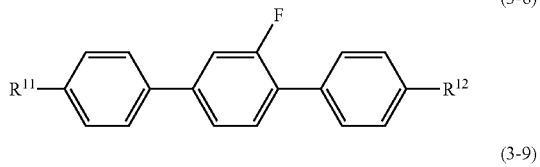

(3-10)
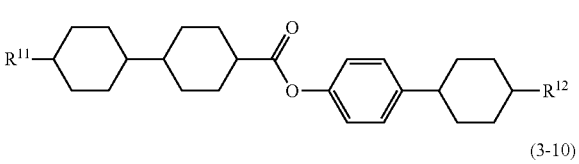

(3-11)
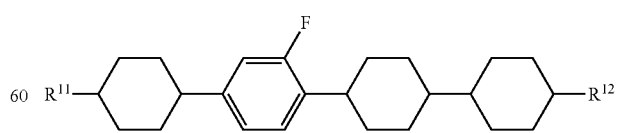

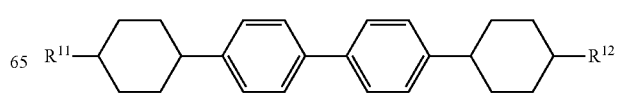

-continued (3-12)

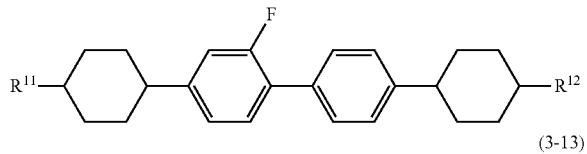

(3-13)

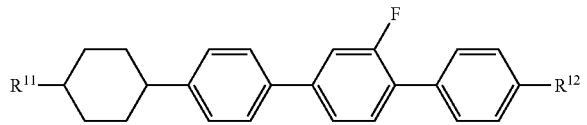

wherein, in formula (3-1) to formula (3-13), $R^{11}$ or $R^{12}$ is independently alkyl having 1 to 12 carbons, alkoxy having 1 to 12 carbons, alkenyl having 2 to 12 carbons, or alkenyl having 2 to 12 carbons in which at least one of hydrogen is replaced by fluorine.

Item 12. The liquid crystal composition according to item 10 or 11, wherein a ratio of the second component is in the range of 10% by weight to 90% by weight based on the weight of the liquid crystal composition.

Item 13. The liquid crystal composition according to any one of Items 1 to 12, further containing at least one polymerizable compound selected from the group of compounds represented by formula (4):

(4)

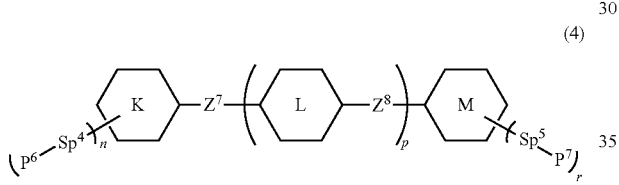

wherein, in formula (4), $P^6$ or $P^7$ is independently a polymerizable group selected from the group of groups represented by formula (P-4) or formula (P-5):

(P-4)

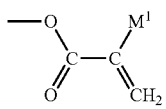

(P-5)

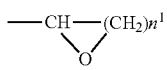

wherein, in formula (P-4), $M^1$ is hydrogen, fluorine, methyl or trifluoromethyl; and in formula (P-5), $n^1$ is 1, 2, 3 or 4;

in formula (4), $Sp^4$ or $Sp^5$ is independently a single bond or alkylene having 1 to 12 carbons, in the alkylene, at least one of —CH$_2$— may be replaced by —O—, —S—, —NH—, —CO—, —COO—, —OCO— or —OCOO—, at least one of —CH$_2$—CH$_2$— may be replaced by —CH═CH— or —C≡C—, and in the groups, at least one of hydrogen may be replaced by halogen or —C≡N; $Z^7$ is a single bond, —CH$_2$CH$_2$—, —CH$_2$O—, —OCH$_2$—, —COO—, —OCO—, —CO—CR$^{13}$═CR$^{14}$—, —R$^{14}$═CR$^{13}$—CO—, —OCO—CR$^{13}$═CR$^{14}$—, —CR$^{14}$═CR$^{13}$—COO—, —CR$^{13}$═CR$^{14}$— or —C(═CR$^{13}$R$^{14}$)—, in which R$^{13}$ or R$^{14}$ is independently hydrogen, halogen, alkyl having 1 to 10 carbons, or alkyl having 1 to 10 carbons in which at least one of hydrogen is replaced by fluorine; $Z^8$ is a single bond, —CH$_2$CH$_2$—, —CH$_2$O—, —OCH$_2$—, —COO— or —OCO—; ring K or ring M is independently cyclohexyl, phenyl, 2-fluorophenyl, 3-fluorophenyl, 2,3-difluorophenyl, 2-methylphenyl, 3-methylphenyl, 2-(trifluoromethyl)phenyl, 3-(trifluoromethyl)phenyl or 2-naphthyl; ring L is 1,4-cyclohexylene, 1,4-phenylene, naphthalene-2,6-diyl, 2-fluoro-1,4-phenylene, 2,3-difluoro-1,4-phenylene, 2,5-difluoro-1,4-phenylene, 2-methyl-1,4-phenylene or 2-trifluoromethyl-1,4-phenylene; p is 0, 1 or 2; and n is 1, 2 or 3, r is 1, 2 or 3, and a sum of n and r is 4 or less.

Item 14. The liquid crystal composition according to any one of items 1 to 13, further containing at least one polymerizable compound selected from the group of compounds represented by formula (4-1) to formula (4-26):

(4-1)

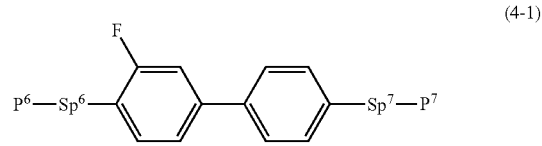

(4-2)

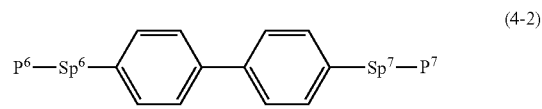

(4-3)

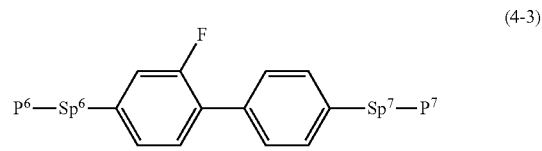

(4-4)

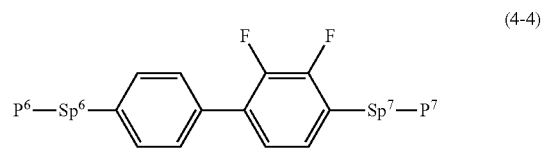

(4-5)

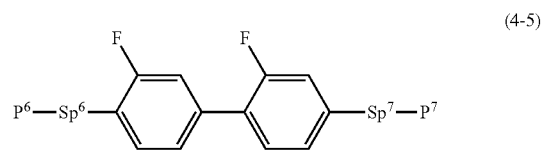

(4-6)

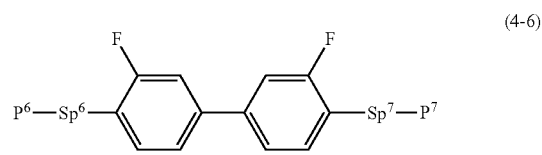

(4-7)

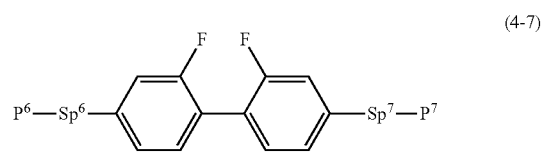

(4-8)

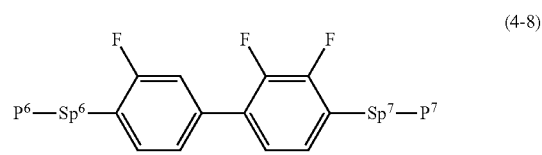

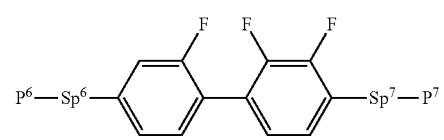
(4-9)
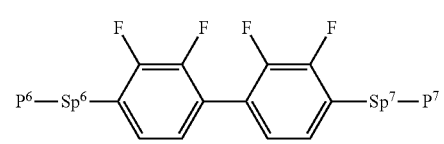
(4-10)
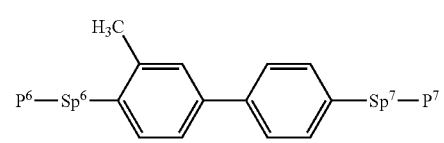
(4-11)
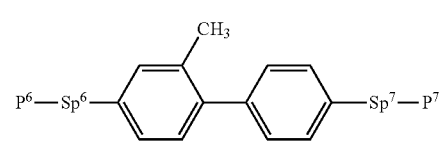
(4-12)
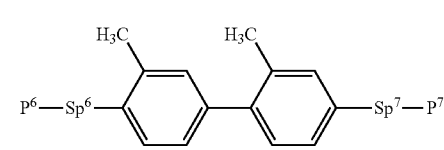
(4-13)
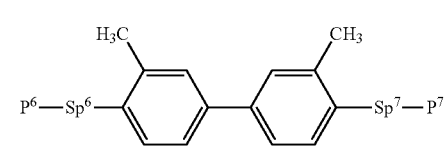
(4-14)
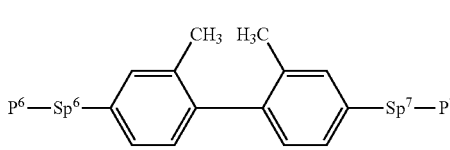
(4-15)
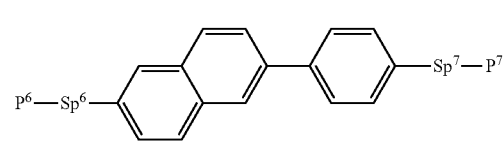
(4-16)
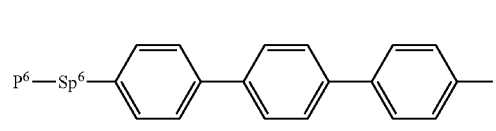
(4-17)
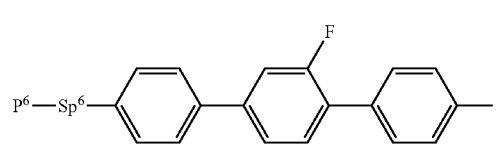
(4-18)
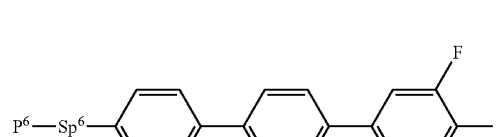
(4-19)
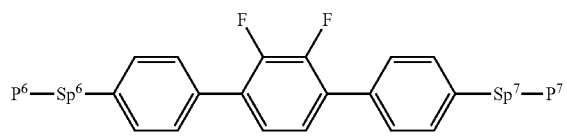
(4-20)
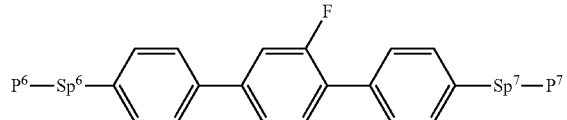
(4-21)
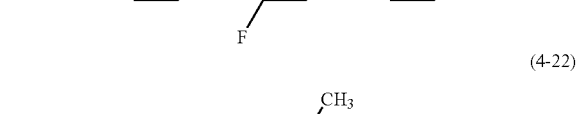
(4-22)
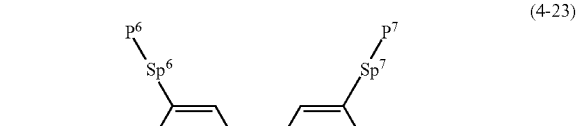
(4-23)
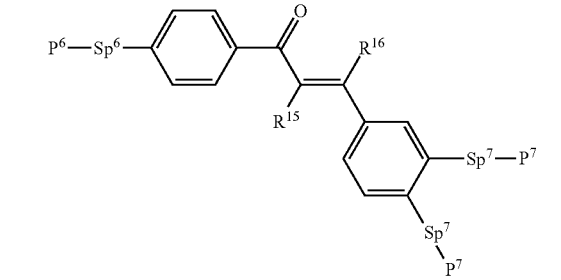
(4-24)
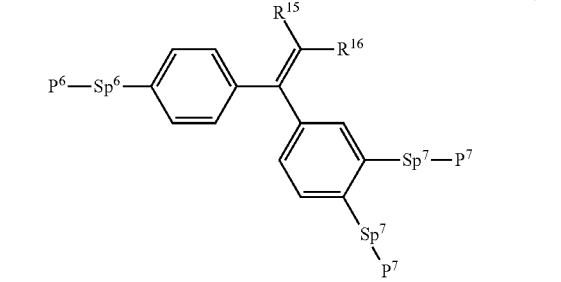
(4-25)
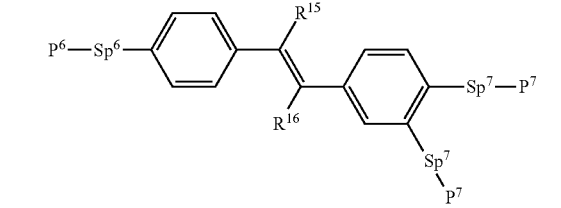
(4-26)
wherein, in formula (4-1) to formula (4-26), $P^6$ or $P^7$ is independently a polymerizable group represented by formula (P-4):

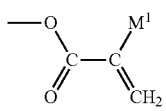

(P-4)

wherein, in formula (P-4), $M^1$ is hydrogen, fluorine, methyl or trifluoromethyl; and in formula (4-1) to formula (4-26), $Sp^6$ or $Sp^7$ is independently a single bond or alkylene having 1 to 12 carbons, in the alkylene, at least one of —$CH_2$— may be replaced by —O—, —COO—, —OCO— or —OCOO—, at least one of —$CH_2$—$CH_2$— may be replaced by —CH=CH— or —C≡C—, and in the groups, at least one of hydrogen may be replaced by fluorine or chlorine; and $R^{15}$ or $R^{16}$ is independently hydrogen, fluorine, chlorine, alkyl having 1 to 3 carbons, or alkyl having 1 to 3 carbons in which at least one of hydrogen is replaced by fluorine.

Item 15. The liquid crystal composition according to any one of items 1 to 14, wherein a ratio of the polymerizable compound is in the range of 0.03% by weight to 10% by weight based on the weight of the liquid crystal composition.

Item 16. The liquid crystal composition according to item 13 or 14, wherein a ratio of the compound represented by formula (1) and the compound represented by formula (4) in the combination is in the range of 0.03% by weight to 10% by weight based on the weight of the liquid crystal composition.

Item 17. A liquid crystal display device, including the liquid crystal composition according to any one of items 1 to 16.

Item 18. The liquid crystal display device according to item 17, wherein an operating mode in the liquid crystal display device includes an IPS mode, a VA mode, an FFS mode or an FPA mode, and a driving mode in the liquid crystal display device includes an active matrix mode.

Item 19. A liquid crystal display device having a polymer sustained alignment mode, wherein the liquid crystal display device includes the liquid crystal composition according to any one of items 1 to 16, and a polymerizable compound in the liquid crystal composition is polymerized.

Item 20. Use of the liquid crystal composition according to any one of items 1 to 16 in a liquid crystal display device.

Item 21. Use of the liquid crystal composition according to any one of items 1 to 16 in a liquid crystal display device having a polymer sustained alignment mode.

The invention further includes the following items: (a) a method of manufacturing the liquid crystal display device by arranging the liquid crystal composition between two substrates, irradiating the composition with light in a state in which voltage is applied to the composition, and polymerizing the polymerizable compound contained in the composition; and (b) the liquid crystal composition having the maximum temperature of the nematic phase is 70° C. or higher, an optical anisotropy (measured at 25° C.) at a wavelength of 589 nanometers is 0.08 or more and a dielectric anisotropy (measured at 25° C.) at a frequency of 1 kHz is less than −2.

The invention further includes the following items: (c) the composition containing at least one compound selected from the group of compound (5) to compound (7) having a positive dielectric anisotropy as described in JP 2006-199941 A; (d) the composition containing polymerizable compound (1); (e) the composition containing polymerizable compound (1) and compound (4); (f) the composition containing a polymerizable compound different from polymerizable compound (1) and polymerizable compound (4); (g) the composition, further containing at least one of additives such as an optically active compound, an antioxidant, an ultraviolet light absorber, a dye, an antifoaming agent, a polymerization initiator or a polymerization inhibitor; (h) an AM device including the composition; (i) a device including the composition and having a TN mode, an ECB mode, an OCB mode, an IPS mode, an FFS mode, a VA mode or an FPA mode; (j) a transmissive device including the composition; (k) use of the composition as a composition having the nematic phase; and (i) use as an optically active composition by adding the optically active compound to the composition.

The composition of the invention will be described in the following order. First, a constitution of component compounds in the composition will be described. Second, main characteristics of the component compounds and main effects of the compounds on the composition will be described. Third, a combination of components in the composition, a preferred ratio of the components and the basis thereof will be described. Fourth, a preferred embodiment of the component compounds will be described. Fifth, a preferred specific examples of the component compounds will be shown. Sixth, an additive that may be added to the composition will be described. Seventh, methods for synthesizing the component compounds will be described. Last, an application of the composition will be described.

First, the constitution of the component compounds in the composition will be described. The composition of the invention is classified into composition A and composition B. Composition A may further contain any other liquid crystal compound, additive or the like in addition to the liquid crystal compound selected from compound (2) or compound (3).

An expression "any other liquid crystal compound" means a liquid crystal compound different from compound (2) or compound (3). Such a compound is mixed with the composition for the purpose of further adjusting the characteristics. Of other liquid crystal compounds, a ratio of a cyano compound is preferably as small as possible in view of stability to heat or ultraviolet light. A further preferred ratio of the cyano compound is 0% by weight. The additive is the optically active compound, the antioxidant, the ultraviolet light absorber, the dye, the antifoaming agent, the polymerizable compound, the polymerization initiator, the polymerization inhibitor or the like.

Composition B consists essentially of liquid crystal compounds selected from compound (2) and compound (3). An expression "essentially" means that the composition may contain the additive such as the polymerizable compound, but contains no any other liquid crystal compound. Composition B has a smaller number of components than composition A has. Composition B is preferred to composition A in view of cost reduction. Composition A is preferred to composition B in view of possibility of further adjusting physical properties by mixing any other liquid crystal compound.

Second, the main characteristics of the component compounds and the main effects of the compounds on the composition will be described. The main characteristics of the component compounds are summarized in Table 2 on the basis of advantageous effects of the invention. In Table 2, a symbol L stands for "large" or "high," a symbol M stands for "medium" and a symbol S stands for "small" or "low." The symbols L, M and S represent a classification based on a qualitative comparison among the component compounds, and 0 (zero) means "a value is nearly zero."

TABLE 2

| Characteristics of Compounds | | |
| --- | --- | --- |
| Compounds | Compound (2) | Compound (3) |
| Maximum Temperature | S to M | S to L |
| Viscosity | L | S to M |
| Optical Anisotropy | M to L | S to L |
| Dielectric Anisotropy | L[1)] | 0 |
| Specific Resistance | L | L |

[1)]A value of dielectric anisotropy is negative, and the symbol shows magnitude of an absolute value Upon mixing the component compounds with the composition, the main effects of the component compounds on the characteristics of the composition are as described below. Compound (1) and compound (4) are polymerized to give a polymer, and the polymer shortens a response time of the device, and improves image persistence. Compound (2) as the first component increases the dielectric anisotropy and decreases a minimum temperature. Compound (3) as the second component decreases the viscosity or increases the maximum temperature.

Third, the combination of components in the composition, the preferred ratio of the component compounds and the basis thereof will be described. A preferred combination of components in the composition includes a combination of compound (1) and the first component, a combination of compound (1) and the second component, a combination of compound (1) and the first component and the second component, a combination of compound (1) and the first component and compound (4) or a combination of compound (1) and the first component and the second component and compound (4). A further preferred combination includes a combination of compound (1) and the first component and the second component or a combination of compound (1) and the first component and the second component and compound (4).

The polymerizable compound such as compound (1) or compound (4) is added to the composition for the purpose of adapting the composition to the polymer sustained alignment mode device. A preferred ratio of the additive component is about 0.03% by weight or more in order to align the liquid crystal molecules, and about 10% by weight or less in order to prevent poor display in the device. A further preferred ratio is in the range of about 0.1% by weight to about 2% by weight. A particularly preferred ratio is in the range of about 0.2% by weight to about 1.0% by weight.

A preferred ratio of the first component is about 10% by weight or more for increasing the dielectric anisotropy, and about 90% by weight or less for decreasing the viscosity. A further preferred ratio is in the range of about 20% by weight to about 80% by weight. A particularly preferred ratio is in the range of about 30% by weight to about 70% by weight.

A preferred ratio of the second component is about 10% by weight or more for increasing the maximum temperature or for decreasing the viscosity, and about 90% by weight or less for decreasing the minimum temperature. A further preferred ratio is in the range of about 20% by weight to about 80% by weight. A particularly preferred ratio is in the range of about 30% by weight to about 70% by weight.

The characteristics of the composition described in Table 1 can be adjusted by adjusting the ratio of the component compounds. The characteristics of the composition may be adjusted by mixing any other liquid crystal compound when necessary. A composition having a maximum temperature of about 70° C. or higher can be prepared by such a method. A composition having a maximum temperature of about 75° C. or higher can also be prepared. A composition having a maximum temperature of about 80° C. or higher can also be prepared. A composition having a minimum temperature of about −10° C. or lower can also be prepared by such a method. A composition having a minimum temperature of about −20° C. or lower can also be prepared. A composition having a minimum temperature of about −30° C. or lower can also be prepared.

A composition having optical anisotropy (measured at 25° C.) at a wavelength of 589 nanometers in the range of about 0.09 to about 0.12 can also be prepared by such a method. A composition having optical anisotropy in the range of about 0.08 to about 0.16 can also be prepared. A composition having optical anisotropy in the range of about 0.07 to about 0.20 can also be prepared. A composition having a dielectric anisotropy (measured at 25° C.) of about −1.5 or less at a frequency of 1 kHz can also be prepared by such a method. A composition having a dielectric anisotropy of about −2 or less can also be prepared. A composition having a dielectric anisotropy of about −2.5 or less can also be prepared.

Fourth, the preferred embodiment of the component compounds will be described. The polymerizable compound described in item 1 has at least two polymerizable groups in which at least one polymerizable group is acryloyloxy or methacryloyloxy, and at least one polymerizable group is a polymerizable group selected from the group of groups represented by formula (P-1), formula (P-2) or formula (P-3):

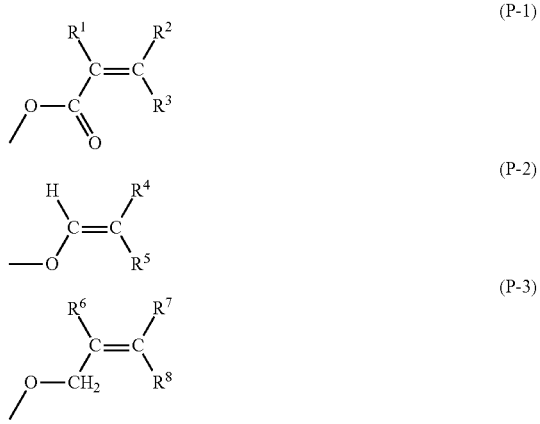

wherein, $R^1$, $R^2$, $R^3$, $R^4$, $R^5$, $R^6$, $R^7$ or $R^8$ is independently hydrogen, fluorine, alkyl having 1 to 5 carbons, or alkyl having 1 to 5 carbons in which at least one of hydrogen is replaced by halogen, when $R^1$ is hydrogen or methyl, at least one of $R^2$ and $R^3$ is fluorine, alkyl having 1 to 5 carbons, or alkyl having 1 to 5 carbons in which at least one of hydrogen is replaced by halogen, at least one of $R^4$ and $R^5$ is fluorine, alkyl having 1 to 5 carbons, or alkyl having 1 to 5 carbons in which at least one of hydrogen is replaced by halogen, at least one of $R^6$, $R^7$ and $R^8$ is fluorine, alkyl having 1 to 5 carbons, or the alkyl having 1 to 5 carbons in which at least one of hydrogen is replaced by halogen. Preferred alkyl is methyl, and preferred alkyl in which at least one of hydrogen is replaced by halogen is trifluoromethyl. Preferred $R^1$, $R^2$, $R^3$, $R^4$, $R^5$, $R^6$, $R^7$ or $R^8$ is hydrogen, fluorine or methyl.

Preferred examples of the polymerizable group represented by formula (P-1), formula (P-2) or formula (P-3) include 2-butenoyloxy(—OCO—CH=CH—CH$_3$), 2-methyl-2-butenoyloxy(—OCO—C(CH$_3$)=CH—CH$_3$), 2-methylenebutanoyloxy(—OCO—C(=CH$_2$)—CH$_2$—CH$_3$), 2-methyl-1-propenyloxy(—O—CH=C(CH$_3$)$_2$), 2,2-difluorovinyloxy(—O—CH=CF$_2$), 2-butenyloxy(—O—CH$_2$—CH=CH—CH$_3$), 2-methyl-2-butenyloxy(—O—CH$_2$—C(CH$_3$)=CH—CH$_3$) or 2-methyl-2-propenyloxy(—O—CH$_2$—C(CH$_3$)=CH$_2$). Then, 2-butenyloxy and 2-methyl-2-propenyloxy are preferred from a viewpoint of a suitable pretilt angle.

In formula (1), ring $A^1$ or ring $C^1$ is independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one of hydrogen may be replaced by halogen, alkyl having 1 to 12 carbons, or alkyl having 1 to 12 carbons in which at least one of hydrogen is replaced by halogen. Preferred ring $A^1$ or ring $C^1$ is phenyl. Ring $B^1$ is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one of hydrogen may be replaced by halogen, alkyl having 1 to 12 carbons, or alkyl having 1 to 12 carbons in which at least one of hydrogen may be replaced by halogen. Preferred ring $B^1$ is 1,4-phenylene, naphthalene-2,6-diyl, 2-fluoro-1,4-phenylene, 2,3-difluoro-1,4-phenylene or 2-methyl-1,4-phenylene. Further preferred ring $B^1$ is 1,4-phenylene.

$Z^1$ or $Z^2$ is independently a single bond or alkylene having 1 to 10 carbons, in the alkylene, at least one of —CH$_2$— may be replaced by —O—, —CO—, —COO— or —OCO—, at least one of —CH$_2$—CH$_2$— may be replaced by —CH=CH—, —C(CH$_3$)=CH—, —CH=C(CH$_3$)— or —C(CH$_3$)=C(CH$_3$)—, and in the groups, at least one of hydrogen may be replaced by fluorine or chlorine. Preferred $Z^1$ or $Z^2$ is a single bond, —CH$_2$CH$_2$—, —CH$_2$O—, —OCH$_2$—, —COO— or —OCO—. Further preferred $Z^1$ or $Z^2$ is a single bond.

At least one of $P^1$, $P^2$ and $P^3$ is acryloyloxy or methacryloyloxy, and at least one remainder is 2-butenyloxy, 2-methyl-2-butenyloxy, 2-methylenebutanoyloxy, 2-methyl-1-propenyloxy, 2,2-difluorovinyloxy, 2-butenyloxy, 2-methyl-2-butenyloxy or 2-methyl-2-propenyloxy. Preferred $P^1$, $P^2$ or $P^3$ is acryloyloxy or methacryloyloxy for increasing reactivity, and 2-butenyloxy or 2-methyl-2-propenyloxy for giving the suitable pretilt angle.

$Sp^1$, $Sp^2$ or $Sp^3$ is independently a single bond or alkylene having 1 to 10 carbons, in the alkylene, at least one of —CH$_2$— may be replaced by —O—, —COO—, —OCO— or —OCOO—, at least one of —CH$_2$—CH$_2$— may be replaced by —CH=CH— or —C≡C—, and in the groups, at least one of hydrogen may be replaced by fluorine or chlorine. Preferred $Sp^1$, $Sp^2$ or $Sp^3$ is a single bond.

Then, a is 0, 1 or 2; b, c or d is independently an integer from 0 to 4, and a sum of b, c and d is 2 or more. Preferred a is 0 or 1. Preferred b or d is 0, 1 or 2. Preferred c is 1 or 2. Then, f, g, h and i each are 0 or 1, and a sum of c, f, g, h and i is 1 or more. Preferred f, g, h or i is 0.

In formula (2) or formula (3), $R^9$ or $R^{10}$ is independently alkyl having 1 to 12 carbons, alkoxy having 1 to 12 carbons, alkenyl having 2 to 12 carbons or alkenyloxy having 2 to 12 carbons. Preferred $R^9$ or $R^{10}$ is alkyl having 1 to 12 carbons for increasing stability, and alkoxy having 1 to 12 carbons for increasing the dielectric anisotropy. $R^{11}$ or $R^{12}$ is independently alkyl having 1 to 12 carbons, alkoxy having 1 to 12 carbons, alkenyl having 2 to 12 carbons, or alkenyl having 2 to 12 carbons in which at least one of hydrogen is replaced by fluorine. Preferred $R^{11}$ or $R^{12}$ is alkenyl having 2 to 12 carbons for decreasing the viscosity or alkyl having 1 to 12 carbons for increasing the stability.

Preferred alkyl is methyl, ethyl, propyl, butyl, pentyl, hexyl, heptyl or octyl. Further preferred alkyl is ethyl, propyl, butyl, pentyl or heptyl for decreasing the viscosity.

Preferred alkoxy is methoxy, ethoxy, propoxy, butoxy, pentyloxy, hexyloxy or heptyloxy. Further preferred alkoxy is methoxy or ethoxy for decreasing the viscosity.

Preferred alkenyl is vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl or 5-hexenyl. Further preferred alkenyl is vinyl, 1-propenyl, 3-butenyl or 3-pentenyl for decreasing the viscosity. A preferred configuration of —CH=CH— in alkenyl depends on a position of a double bond. Trans is preferred in alkenyl such as 1-propenyl, 1-butenyl, 1-pentenyl, 1-hexenyl, 3-pentenyl or 3-hexenyl for decreasing the viscosity and so forth. Cis is preferred in alkenyl such as 2-butenyl, 2-pentenyl or 2-hexenyl.

Preferred alkenyloxy is vinyloxy, allyloxy, 3-butenyloxy, 3-pentenyloxy or 4-pentenyloxy. Further preferred alkenyloxy is allyloxy or 3-butenyloxy for decreasing the viscosity.

Preferred examples of alkenyl in which at least one of hydrogen is replaced by fluorine include 2,2-difluorovinyl, 3,3-difluoro-2-propenyl, 4,4-difluoro-3-butenyl, 5,5-difluoro-4-pentenyl or 6,6-difluoro-5-hexenyl. Further preferred examples include 2,2-difluorovinyl or 4,4-difluoro-3-butenyl for decreasing the viscosity.

Alkyl has a straight chain or a branched chain and contains no cyclic alkyl. Straight-chain alkyl is preferred to branched-chain alkyl. A same rule applies also to alkoxy, alkenyl, and alkenyl in which at least one of hydrogen is replaced by fluorine. According to a configuration of 1,4-cyclohexylene, trans is preferred to cis for increasing the maximum temperature.

Ring D or ring F is independently 1,4-cyclohexylene, 1,4-phenylene, 1,4-phenylene in which at least one of hydrogen is replaced by fluorine or chlorine or tetrahydropyran-2,5-diyl. Preferred ring D or ring F is 1,4-cyclohexylene for decreasing the viscosity, tetrahydropyran-2,5-diyl for increasing the dielectric anisotropy, and 1,4-phenylene for increasing the optical anisotropy. With regard to the configuration of 1,4-cyclohexylene, trans is preferred to cis for increasing the maximum temperature. Tetrahydropyran-2,5-diyl includes:

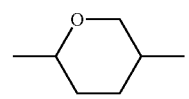

or

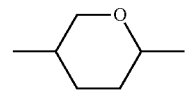, preferably

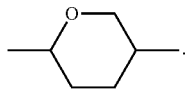

Ring E is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl. Preferred ring E is 2,3-difluoro-1,4-phenylene for decreasing the viscosity, 2-chloro-3-fluoro-1,4-phenylene for decreasing the optical anisotropy, and 7,8-difluorochroman-2,6-diyl for increasing the dielectric anisotropy.

Ring G, ring I or ring J is independently 1,4-cyclohexylene, 1,4-phenylene or 2-fluoro-1,4-phenylene. Preferred ring G, ring I or ring J is 1,4-cyclohexylene for decreasing the viscosity or for increasing the maximum temperature, and 1,4-phenylene for decreasing the minimum temperature.

$Z^3$, $Z^4$, $Z^5$ or $Z^6$ is independently a single bond, —CH$_2$CH$_2$—, —CH$_2$O—, —OCH$_2$—, —COO— or —OCO—. Preferred $Z^3$ or $Z^4$ is a single bond for decreasing the viscosity, —CH$_2$CH$_2$— for decreasing the minimum temperature, and —CH$_2$O— or —OCH$_2$— for increasing the dielectric anisotropy. Preferred $Z^5$ or $Z^6$ is a single bond for decreasing the viscosity, —CH$_2$CH$_2$— for decreasing the minimum temperature, and —COO— or —OCO— for increasing the maximum temperature.

Then, j is 1, 2 or 3. Preferred j is 1 for decreasing the viscosity, and 2 or 3 for increasing the maximum temperature. Then, k is 0 or 1. Preferred k is 0 for decreasing the viscosity, and 1 for decreasing the minimum temperature. Then, m is 0, 1 or 2. Preferred m is 0 for decreasing the viscosity, and 1 or 2 for increasing the maximum temperature.

In formula (4), $P^6$ or $P^7$ is independently a polymerizable group selected from the group of groups represented by formula (P-4) or formula (P-5).

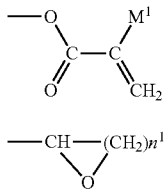

In formula (P-4), $M^1$ is hydrogen, fluorine, methyl or trifluoromethyl. Preferred $M^1$ is hydrogen or methyl for increasing reactivity. Further preferred $M^1$ is methyl. In formula (P-5), $n^1$ is 1, 2, 3 or 4. Preferred $n^1$ is 1 or 2 for increasing reactivity. Further preferred $n^1$ is 1. When both $P^6$ and $P^7$ are a polymerizable group represented by formula (P-4), a group represented by $M^1$ in $P^6$ and a group represented by $M^1$ in $P^7$ may be identical or different.

$Sp^4$ or $Sp^5$ is independently a single bond or alkylene having 1 to 12 carbons, in the alkylene, at least one of —CH$_2$— may be replaced by —O—, —S—, —NH—, —CO—, —COO—, —OCO— or —OCOO—, at least one of —CH$_2$—CH$_2$— may be replaced by —CH═CH— or —C≡C—, and in the groups, at least one of hydrogen may be replaced by halogen or —C≡N. A total of the number of carbons in alkylene in which anyone of hydrogen is replaced by —C≡N is preferably 12 or less. Preferred $Sp^4$ or $Sp^5$ is a single bond.

$Z^7$ is a single bond, —CH$_2$CH$_2$—, —CH$_2$O—, —OCH$_2$—, —COO—, —OCO—, —CO—CR$^{13}$═CR$^{14}$—, —CR$^{14}$═CR$^{13}$—CO—, —OCO—CR$^{13}$═CR$^{14}$—, —CR$^{14}$═CR$^{13}$—COO—, —CR$^{13}$═CR$^{14}$— or —C(═CR$^{13}$R$^{14}$)—, in which R$^{13}$ or R$^{14}$ is independently hydrogen, halogen, alkyl having 1 to 10 carbons, or alkyl having 1 to 10 carbons in which at least one of hydrogen is replaced by fluorine. Preferred R$^{13}$ or R$^{14}$ is hydrogen, fluorine or alkyl having 1 to 3 carbons. $Z^8$ is a single bond, —CH$_2$CH$_2$—, —CH$_2$O—, —OCH$_2$—, —COO— or —OCO—. Preferred $Z^7$ or $Z^8$ is a single bond, —CH$_2$CH$_2$—, —CH$_2$O—, —OCH$_2$—, —COO— or —OCO—. Further preferred $Z^7$ or $Z^8$ is a single bond.

Ring K or ring M is independently cyclohexyl, phenyl, 2-fluorophenyl, 3-fluorophenyl, 2,3-difluorophenyl, 2-methylphenyl, 3-methylphenyl, 2-(trifluoromethyl)phenyl, 3-(trifluoromethyl)phenyl or 2-naphthyl. Preferred ring K or ring M is phenyl. Ring L is 1,4-cyclohexylene, 1,4-phenylene, naphthalene-2,6-diyl, 2-fluoro-1,4-phenylene, 2,3-difluoro-1,4-phenylene, 2,5-difluoro-1,4-phenylene, 2-methyl-1,4-phenylene or 2-trifluoromethyl-1,4-phenylene. Preferred ring L is 1,4-phenylene, naphthalene-2,6-diyl, 2-fluoro-1,4-phenylene, 2,3-difluoro-1,4-phenylene or 2-methyl-1,4-phenylene. Particularly preferred ring L is 1,4-phenylene or 2-fluoro-1,4-phenylene.

Then, p is 0, 1 or 2, n is 1, 2 or 3, r is 1, 2 or 3, and a sum of n and r is 4 or less. Preferred p is 0. Preferred n or r is 1 or 2.

Fifth, the preferred component compounds will be shown. Preferred compound (1) includes compound (1-1) described above. Further preferred compound (1) includes compound (1-1-1) described above. Particularly preferred compound (1) includes compound (1-1-1-1) to compound (1-1-1-12) described above. A preferred composition contains compound (1-1-1-2), compound (1-1-1-3), compound (1-1-1-6), compound (1-1-1-8) or compound (1-1-1-12). A further preferred composition contains compound (1-1-1-2) and compound (1-1-1-3).

Preferred compound (2) includes compound (2-1) to compound (2-19) described above. In the compounds, at least one of the first component preferably includes compound (2-1), compound (2-3), compound (2-4), compound (2-6), compound (2-8) or compound (2-13). At least two of the first component preferably includes a combination of compound (2-1) and compound (2-6), a combination of compound (2-1) and compound (2-13), a combination of compound (2-3) and compound (2-6), a combination of compound (2-3) and compound (2-13) or a combination of compound (2-4) and compound (2-8).

Preferred compound (3) includes compound (3-1) to compound (3-13) described above. In the compounds, at least one of the second component preferably includes compound (3-1), compound (3-3), compound (3-5), compound (3-6), compound (3-7) or compound (3-8). At least two of the second component preferably includes a combination of compound (3-1) and compound (3-3), a combination of compound (3-1) and compound (3-5) or a combination of compound (3-1) and compound (3-6).

Preferred compound (4) includes compound (4-1) to compound (4-26) described above. A preferred composition contains compound (4-1), compound (4-2) or compound (4-18). A further preferred composition contains a combination of compound (4-1) and compound (4-2), a combination of compound (4-1) and compound (4-18) or a combination of compound (4-2) and compound (4-18).

Sixth, the additive that may be added to the composition will be described. The additive is the optically active compound, the antioxidant, the ultraviolet light absorber, the dye, the antifoaming agent, the polymerizable compound, the polymerization initiator, the polymerization inhibitor or the like. The optically active compound is added to the composition for inducing a helical structure in a liquid crystal to give a twist angle. Examples of such a compound include compound (5-1) to compound (5-5). A preferred ratio of the optically active compound is about 5% by weight or less. A further preferred ratio is in the range of about 0.01% by weight to about 2% by weight.

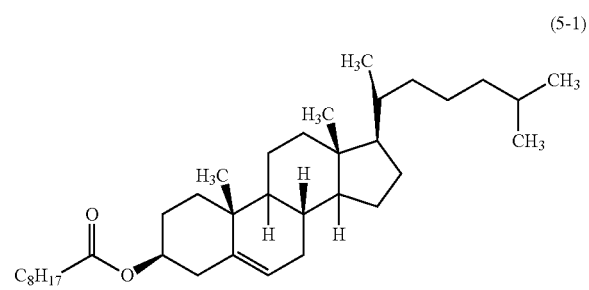

(5-1)

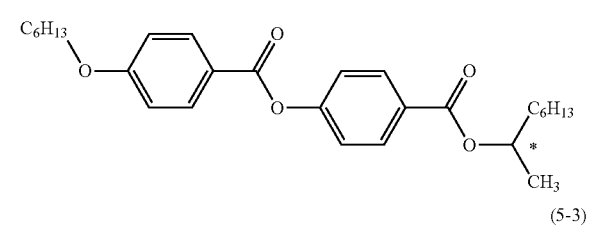

(5-2)

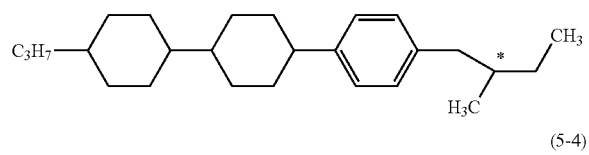

(5-3)

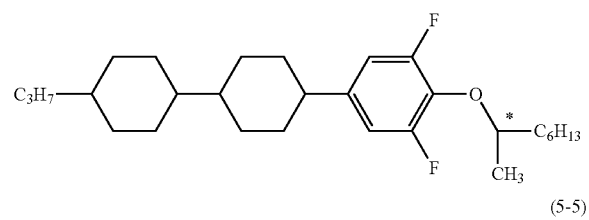

(5-4)

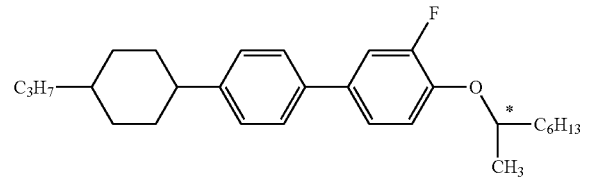

(5-5)

The antioxidant is added to the composition for preventing a decrease in the specific resistance caused by heating in air, or for maintaining a large voltage holding ratio at room temperature and also at the temperature close to the maximum temperature after the device has been used for a long period of time.

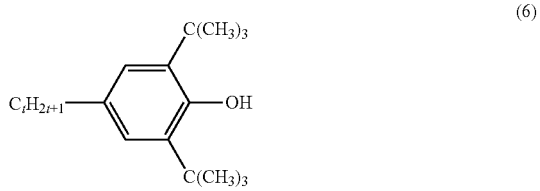

(6)

Preferred examples of the antioxidant include compound (6) where t is an integer 1 to 9 or the like. In compound (6), preferred t is 1, 3, 5, 7 or 9. Further preferred t is 1 or 7. Compound (6) where t is 1 is effective for preventing the decrease in the specific resistance caused by heating in air because the compound (6) has a large volatility. Compound (6) where t is 7 is effective for maintaining the large voltage holding ratio at room temperature and also at the temperature close to the maximum temperature even after the device has been used for a long period of time because the compound (6) has a small volatility. A preferred ratio of the antioxidant is about 50 ppm or more for achieving an effect thereof, and about 600 ppm or less for avoiding a decrease in the maximum temperature or an increase in the minimum temperature. A further preferred ratio is in the range of about 100 ppm to about 300 ppm.

Preferred examples of the ultraviolet light absorber include a benzophenone derivative, a benzoate derivative and a triazole derivative. A light stabilizer such as an amine having steric hindrance is also preferred. A preferred ratio of the absorber or the stabilizer is about 50 ppm or more for achieving an effect thereof, and about 10,000 ppm or less for avoiding the decrease in the maximum temperature or avoiding the increase in the minimum temperature. A further preferred ratio is in the range of about 100 ppm to about 10,000 ppm.

A dichroic dye such as an azo dye or an anthraquinone dye is added to the composition for the purpose of adapting the composition to a device having a guest host (GH) mode. A preferred ratio of the dye is in the range of about 0.01% by weight to about 10% by weight. The antifoaming agent such as dimethyl silicone oil or methyl phenyl silicone oil is added to the composition for preventing foam formation. A preferred ratio of the antifoaming agent is about 1 ppm or more for achieving an effect thereof, and about 1,000 ppm or less for avoiding a poor display. A further preferred ratio is in the range of about 1 ppm to about 500 ppm.

The polymerizable compound is added to the composition for the purpose of adapting the composition to a device having the polymer sustained alignment (PSA) mode. Compound (1) or compound (4) is suitable for the purpose. A polymerizable compound different from compound (1) and compound (4) may be added to the composition together with compound (1) and compound (4). Preferred examples of other polymerizable compounds include a compound such as acrylate, methacrylate, a vinyl compound, a vinyloxy compound, propenyl ether, an epoxy compound (oxirane, oxetane) and vinyl ketone. Further preferred examples include an acrylate derivative or a methacrylate derivative. When adding other polymerizable compounds to the composition, a preferred ratio of compound (1) or a preferred ratio of amounts of compound (1) and compound (5) is about 10% by weight or more based on the total weight of the polymerizable compound. A further preferred ratio is about 50% by weight or more based thereon. A particularly preferred ratio is about 80% by weight or more based thereon. A particularly preferred ratio is also 100% by weight based thereon.

The polymerizable compound such as compound (1) or compound (4) is polymerized by irradiation with ultraviolet light. The polymerizable compound such as compound (6) may be polymerized in the presence of a suitable initiator such as a photopolymerization initiator. Suitable conditions for polymerization, suitable types of the initiator and suitable amounts thereof are known to those skilled in the art and are described in literature. For example, Irgacure 651 (registered trademark; BASF), Irgacure 184 (registered trademark; BASF) or Darocur 1173 (registered trademark; BASF), each being a photoinitiator, is suitable for radical polymerization. A preferred ratio of the photopolymerization initiator is in the range of about 0.1% by weight to about 5% by weight based on the total weight of the polymerizable compound. A further preferred ratio is in the range of about 1% by weight to about 3% by weight based thereon.

Upon storing the polymerizable compound such as compound (1) or compound (4), the polymerization inhibitor may be added thereto for preventing polymerization. The polymerizable compound is ordinarily added to the composition without removing the polymerization inhibitor. Examples of the polymerization inhibitor include hydroquinone and a hydroquinone derivative such as methylhydroquinone, 4-tert-butylcatechol, 4-methoxyphenol or phenothiazine.

Seventh, the methods for synthesizing the component compounds will be described. The compounds are synthesized by a known method. Examples of the synthetic methods are described. Compound (2-1) is prepared by a method described in JP 2000-053602 A. Compound (3-1) or compound (3-5) is prepared by a method described in JP S59-176221 A. Compound (4) is prepared with reference to JP 2012-001526 A and WO 2010-131600 A. Compound (4-18) is prepared by a method described in JP H7-101900 A. The antioxidant is commercially available. A compound where t in formula (6) is 1 can be obtained from Sigma-Aldrich Corporation. A compound where t in compound (6) is 7 or the like can be prepared according to a method described in U.S. Pat. No. 3,660,505 B.

Any compounds whose synthetic methods are not described can be prepared according to methods described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza in Japanese) (Maruzen Co., Ltd.). The composition is prepared according to publicly known methods using the thus obtained compounds. For example, the component compounds are mixed and dissolved in each other by heating.

Last, the application of the composition will be described. The composition of the invention mainly has a minimum temperature of about −10° C. or lower, a maximum temperature of about 70° C. or higher, and an optical anisotropy in the range of about 0.07 to about 0.20. A device including the composition has the large voltage holding ratio. The composition is suitable for use in the AM device. The composition is particularly suitable for use in a transmissive AM device. The composition can be used as the composition having the nematic phase, and as the optically active composition by adding the optically active compound.

The composition can be used for the AM device. The composition can also be used for a PM device. The composition can also be used for the AM device and the PM device each having a mode such as a PC mode, the TN mode, a STN mode, the ECB mode, the OCB mode, the IPS mode, the VA mode and the FPA mode. Use for the AM device having the IPS mode, the FFS mode or the VA mode is particularly preferred. The device may be of a reflective type, a transmissive type or a transflective type. Use for the transmissive device is preferred. Use for an amorphous silicon-TFT device or a polycrystal silicon-TFT device is allowed. By increasing an adding amount of a polymerizable compound, a polymer dispersed (PD) device in which a three-dimensional network-polymer is formed in the composition is allowed.

One example of the method for manufacturing the device having the polymer sustained alignment mode is as described below. A device having two substrates referred to as an array substrate and a color filter substrate is prepared. At least one of the substrates has an electrode layer. The liquid crystal composition is prepared by mixing the liquid crystal compounds. The polymerizable compound is added to the composition. The additive may be further added when necessary. The composition is injected into the device. The device is irradiated with light in a state in which voltage is applied. Irradiation with ultraviolet light is preferred. The polymerizable compound is polymerized by irradiation with light. The composition containing the polymer is formed by the polymerization. The liquid crystal display device having the polymer sustained alignment mode is manufactured in such a procedure.

In the procedure, when voltage is applied, the liquid crystal molecules are aligned due to an effect of an electric field. Molecules of the polymerizable compound are also aligned according to the alignment. The polymerizable compound is polymerized by irradiation with ultraviolet light in the above state, and therefore the polymer in which the alignment is maintained is formed. The response time of the device is shortened due to an effect of the polymer. The image persistence is caused due to poor operation in the liquid crystal molecules, and therefore is to be simultaneously improved by the effect of the polymer. In addition, the polymerizable compound in the composition is previously polymerized, and the composition may be arranged between the substrates in the liquid crystal display device.

EXAMPLES

The invention will be described in greater detail by way of Examples. However, the invention is not limited by the Examples. The invention includes a mixture of a composition in Example 1 and a composition in Example 2. The invention also includes a mixture in which at least two compositions in Examples are mixed. The thus prepared compound was identified by methods such as an NMR analysis. Characteristics of the compound and the composition were measured by methods described below.

NMR analysis: For measurement, DRX-500 made by Bruker BioSpin Corporation was used. In $^1$H-NMR measurement, a sample was dissolved in a deuterated solvent such as $CDCl_3$, and measurement was carried out under conditions of room temperature, 500 MHZ and 16 times of accumulation. Tetramethylsilane (TMS) was used as an internal standard. In $^{19}$F-NMR measurement, $CFCl_3$ was used as an internal standard, and measurement was carried out under conditions of 24 times of accumulation. In explaining nuclear magnetic resonance spectra obtained, s, d, t, q, quin, sex, m and r stand for a singlet, a doublet, a triplet, a quartet, a quintet, a sextet, a multiplet, and br being broad, respectively.

Gas chromatographic analysis: GC-14B Gas Chromatograph made by Shimadzu Corporation was used for measurement. A carrier gas was helium (2 mL/per minute). A sample injector and a detector (FID) were set to 280° C. and 300° C., respectively. A capillary column DB-1 (length 30 m, bore 0.32 mm, film thickness 0.25 μm; dimethylpolysiloxane as a stationary phase, non-polar) made by Agilent Technologies, Inc. was used for separation of component compounds. After the column was kept at 200° C. for 2 minutes, the column was heated to 280° C. at a rate of 5° C. per minute. A sample was prepared in an acetone solution (0.1% by weight), and then 1 microliter of the solution was injected into the sample injector. A recorder was C-R5A Chromatopac made by Shimadzu Corporation or the equivalent thereof. The resulting gas chromatogram showed a retention time of a peak and a peak area corresponding to each of the component compounds.

As a solvent for diluting the sample, chloroform, hexane or the like may also be used. The following capillary columns may also be used for separating component compounds: HP-1 (length 30 m, bore 0.32 mm, film thickness 0.25 μm) made by Agilent Technologies, Inc., Rtx-1 (length 30 m, bore 0.32 mm, film thickness 0.25 μm) made by Restek Corporation and BP-1 (length 30 m, bore 0.32 mm, film thickness 0.25 μm) made by SGE International Pty. Ltd. A capillary column CBP1-M50-025 (length 50 m, bore 0.25 mm, film thickness 0.25 μm) made by Shimadzu Corporation may also be used for the purpose of avoiding an overlap of peaks of the compounds.

A ratio of liquid crystal compounds contained in the composition may be calculated by the method as described below. The mixture of liquid crystal compounds is detected by gas chromatograph (FID). An area ratio of each peak in the gas chromatogram corresponds to the ratio (weight ratio) of the liquid crystal compound. When the capillary columns described above were used, a correction coefficient of each of the liquid crystal compounds may be regarded as 1 (one). Accordingly, the ratio (% by weight) of the liquid crystal compound is calculated from the area ratio of each peak.

Sample for measurement: When characteristics of a composition was measured, the composition was used as a sample as was. Upon measuring characteristics of a compound, a sample for measurement was prepared by mixing the compound (15% by weight) with a base liquid crystal (85% by weight). Values of characteristics of the compound were calculated, according to an extrapolation method, using values obtained by measurement. (Extrapolated value)= {(measured value of a sample for measurement)−0.85× (measured value of a base liquid crystal)}/0.15. When a smectic phase (or crystals) precipitates at the ratio thereof at 25° C., a ratio of the compound to the base liquid crystal was changed step by step in the order of (10% by weight:90% by weight), (5% by weight:95% by weight) and (1% by weight: 99% by weight). Values of maximum temperature, optical anisotropy, viscosity and dielectric anisotropy with regard to the compound were determined according to the extrapolation method.

A base liquid crystal described below was used. A ratio of the component compound was expressed in terms of weight percent (% by weight).

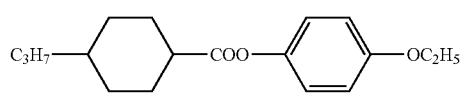

17.2%

-continued

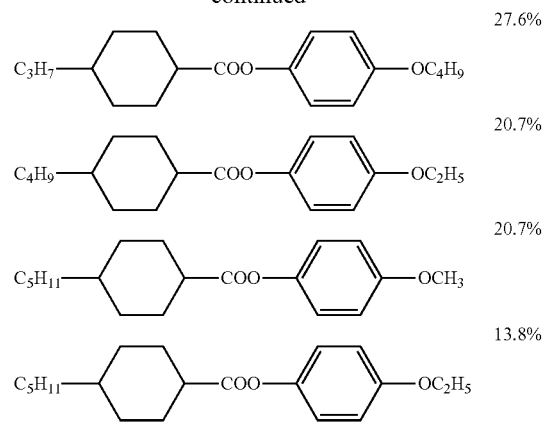

Measuring method: Measurement of characteristics was carried out by the methods described below. Most of the measuring methods are applied as described in the Standard of the Japan Electronics and Information Technology Industries Association (hereinafter abbreviated as JEITA) (JEITA EIAJ ED-2521B) discussed and established by JEITA, or modified thereon. No thin film transistor (TFT) was attached to a TN device used for measurement.

(1) Maximum temperature of nematic phase (NI; ° C.): A sample was placed on a hot plate in a melting point apparatus equipped with a polarizing microscope, and heated at a rate of 1° C. per minute. Temperature when part of the sample began to change from a nematic phase to an isotropic liquid was measured. A higher limit of a temperature range of the nematic phase may be occasionally abbreviated as "Maximum temperature."

(2) Minimum temperature of nematic phase ($T_c$; ° C.): Samples each having a nematic phase were put in glass vials and kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., Tc of the sample was expressed as $T_c$<−20° C. A minimum temperature of the nematic phase may be occasionally abbreviated as "minimum temperature."

(3) Viscosity (bulk viscosity; η; measured at 20° C.; mPa·s): A cone-plate (E type) rotational viscometer made by Tokyo Keiki, Inc. was used for measurement.

(4) Viscosity (rotational viscosity; γ1; measured at 25° C.; mPa·s): Measurement was carried out according to a method described in M. Imai et al., Molecular Crystals and Liquid Crystals, Vol. 259, p. 37 (1995). A sample was put in a VA device in which a distance (cell gap) between two glass substrates was 20 micrometers. Voltage was applied stepwise to the device in the range of 39 V to 50 V at an increment of 1 V. After a period of 0.2 second with no voltage application, voltage was applied repeatedly under the conditions of only one rectangular wave (rectangular pulse; 0.2 second) and no voltage application (2 seconds). A peak current and a peak time of a transient current generated by the applied voltage were measured. A value of rotational viscosity was obtained from the measured values and a calculation equation (8) described on page 40 of the paper presented by M. Imai et al. A dielectric anisotropy required for the calculation was measured according to section (6) described below.

(5) Optical anisotropy (refractive index anisotropy; Δn; measured at 25° C.): Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when a direction of polarized light was parallel to a direction of rubbing. A refractive index (n⊥) was measured when the direction of polarized light was perpendicular to the direction of rubbing. A value of optical anisotropy was calculated from an equation: Δn=n∥−n⊥.

(6) Dielectric anisotropy (Δ∈; measured at 25° C.): A value of dielectric anisotropy was calculated from an equation: Δ∈=∈∥−∈⊥. A dielectric constant (∈∥ and ∈⊥) was measured as described below.

1) Measurement of dielectric constant (∈∥): An ethanol (20 mL) solution of octadecyl triethoxysilane (0.16 mL) was applied to a well-cleaned glass substrate. After rotating the glass substrate with a spinner, the glass substrate was heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (∈∥) in a major axis direction of liquid crystal molecules was measured.

2) Measurement of dielectric constant (∈⊥): A polyimide solution was applied to a well-cleaned glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant (∈⊥) in a minor axis direction of the liquid crystal molecules was measured.

(7) Threshold voltage ($V_{th}$; measured at 25° C.; V): An LCD-5100 luminance meter made by Otsuka Electronics Co., Ltd. was used for measurement. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. A voltage (60 Hz, rectangular waves) to be applied to the device was stepwise increased from 0 V to 20 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage is expressed in terms of a voltage at 10% transmittance.

(8) Voltage holding ratio (VHR-1a; measured at 25° C.; %): A TN device used for measurement had a polyimide alignment film, and a distance (cell gap) between two glass substrates was 5 micrometers. A sample was put in the device, and the device was sealed with an ultraviolet-curable adhesive. A pulse voltage (60 microseconds at 5 V) was applied to the TN device and the device was charged. A decaying voltage was measured for 166.7 milliseconds with a high-speed voltmeter, and area A between a voltage curve and a horizontal axis in a unit cycle was determined. Area B is an area without decay. A voltage holding ratio is expressed in terms of a percentage of area A to area B.

(9) Voltage holding ratio (VHR-2a; measured at 60° C.; %): A voltage holding ratio was measured according to procedures identical with the procedures described above except that measurement was carried out at 60° C. in place of 25° C. The thus obtained value was expressed in terms of VHR-2a. In a composition containing a polymerizable compound, a TN devise including the composition was irradiated with ultraviolet light of 25 mW/cm$^2$ for 400 seconds while applying a voltage of 15V to the TN device, and the polymerizable compound in the composition was polymerized. An EXECURE 4000-D type Mercury-Xenon lamp made from HOYA CANDEO OPTRONICS CORPORATION was used for irradiation of ultraviolet light.

(10) Voltage holding ratio (VHR-3a; measured at 60° C.; %): Stability to ultraviolet light was evaluated by measuring a voltage holding ratio after a device was irradiated with ultraviolet light. A TN device used for measurement had a polyimide alignment film and a cell gap was 5 micrometers. A sample was injected into the device, and then the device was irradiated with light for 167 minutes. A light source was black light (peak wavelength of 369 nm), and a distance between the device and the light source was 5 millimeters. In measurement of VHR-3a, a decaying voltage was measured for 166.7 milliseconds. A composition containing a polymerizable compound was polymerized on condition described in (9) item. A composition having large VHR-3a has a large stability to ultraviolet light.

(11) Voltage holding ratio (VHR-4a; measured at 25° C.; %): Stability to heat was evaluated by measuring a voltage holding ratio after a TN device into which a sample was injected was heated in a constant-temperature bath at 80° C. for 500 hours. In measurement of VHR-4a, a decaying voltage was measured for 166.7 milliseconds. A composition having large VHR-4a has a large stability to heat.

(12) Response Time (τ; measured at 25° C.; ms): An LCD-5100 luminance meter made by Otsuka Electronics Co., Ltd. was used for measurement. A light source was a halogen lamp. A low-pass filter was set at 5 kHz.

1) A composition containing no polymerizable compound: A sample was put in a normally black mode VA device in which a distance (cell gap) between two glass substrates was 4 micrometers and a rubbing direction was anti-parallel. The device was sealed with an ultraviolet-curable adhesive. A voltage (rectangular waves; 60 Hz, 10V, 0.5 second) was applied to the device. On the occasion, the device was irradiated with light from a direction perpendicular to the device, and an amount of light transmitted through the device was measured: A voltage-transmittance curve was prepared, in which the maximum amount of light corresponds to 100% transmittance and the minimum amount of light corresponds to 0% transmittance. A response time was expressed in terms of time required for a change from 90% transmittance to 10% transmittance (fall time; millisecond).

2) A composition containing a polymerizable compound: A sample was put in a normally black mode PVA device in which a distance (cell gap) between two glass substrates was 3.2 micrometers and a rubbing direction was anti-parallel. The device was sealed with an ultraviolet-curable adhesive. The device was irradiated with ultraviolet light of 25 mW/cm$^2$ for 400 seconds while applying a voltage of 15V to the device. The EXECURE 4000-D type Mercury-Xenon lamp made from HOYA CANDEO OPTRONICS CORPORATION was used for irradiation of ultraviolet light. Rectangular waves (60 Hz, 10V, 0.5 second) were applied to the device. On the occasion, the device was irradiated with light from a direction perpendicular to the device, and an amount of light transmitted through the device was measured: A voltage-transmittance curve was prepared, in which the maximum amount of light corresponds to 100% transmittance and the minimum amount of light corresponds to 0% transmittance. A response time was expressed in terms of time required for a change from 0% transmittance to 90% transmittance (rise time; millisecond).

(13) Specific resistance (ρ; measured at 25 C; Ωcm): Into a vessel equipped with electrodes, 1.0 mL of a sample was injected. A direct current voltage (10V) was applied to the vessel, and a direct current after 10 seconds was measured: Specific resistance was calculated from the following equation: (specific resistance)={(voltage)×(electric capacity of the vessel)}/{(direct current)×(dielectric constant of vacuum)}.

The compounds described in Comparative Examples and Examples were described using symbols according to definitions in Table 3 below. In Table 3, the configuration of 1,4-cyclohexylene is trans. A parenthesized number next to a symbolized compound in Examples corresponds to the number of the compound. A symbol (-) means any other liquid crystal compound. A ratio (percentage) of the liquid crystal compound is expressed in terms of weight percent (% by weight) based on the weight of the liquid crystal composition.

TABLE 3

Method for Description of Compounds using Symbols
R—(A$_1$)—Z$_1$—····—Z$_n$—(A$_n$)—R'

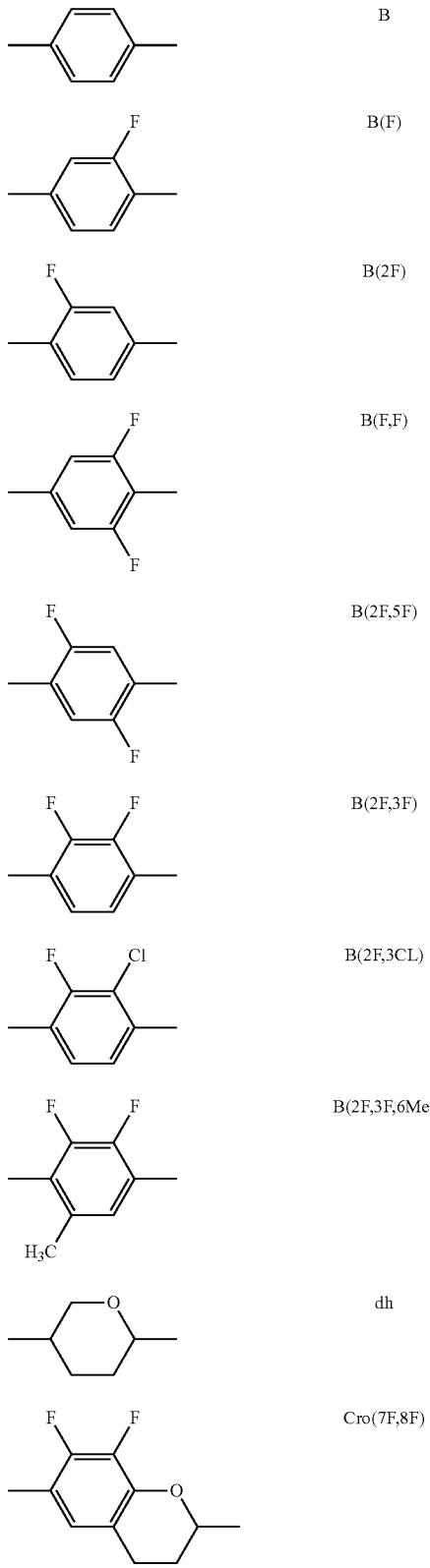

TABLE 3-continued

Method for Description of Compounds using Symbols $$R-(A_1)-Z_1-\cdots-Z_n-(A_n)-R'$$

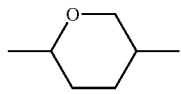  Dh

5) Examples of Description

Example 1  2-BB(F)B-3

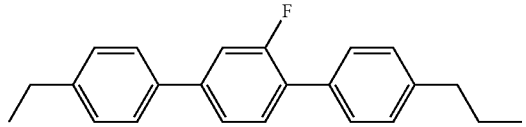 [SMILES: CCCc1ccc(-c2ccc(-c3ccc(CC)cc3)cc2F)cc1]

Example 2  MAC-BB-MAC

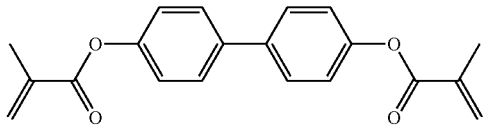 [SMILES: C=C(C)C(=O)Oc1ccc(-c2ccc(OC(=O)C(=C)C)cc2)cc1]

Example 3  V-HHB-1

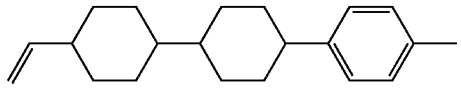

Example 4  3-HDhB(2F,3F)-O2

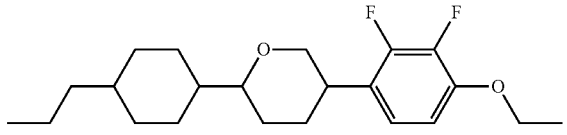 [SMILES: CCCC1CCC(C2CCC(c3ccc(OCC)c(F)c3F)CO2)CC1]

Example 1

| | | |
|---|---|---|
| 3-H1OB(2F,3F)-O2 | (2-3) | 4% |
| V2-BB(2F,3F)-O1 | (2-4) | 5% |
| V2-BB(2F,3F)-O2 | (2-4) | 9% |
| 1V2-BB(2F,3F)-O2 | (2-4) | 6% |
| V-HHB(2F,3F)-O1 | (2-6) | 3% |
| V-HHB(2F,3F)-O2 | (2-6) | 10% |
| 3-HH1OB(2F,3F)-O2 | (2-8) | 11% |
| 2-BB(2F,3F)B-3 | (2-9) | 9% |
| 3-HH-V | (3-1) | 27% |
| 3-HH-V1 | (3-1) | 9% |
| 3-HHB-O1 | (3-5) | 3% |
| V-HHB-1 | (3-5) | 4% |

A composition having negative dielectric anisotropy was prepared, and characteristics thereof were measured: NI=75.6° C.; $T_c$<−20° C.; Δn=0.111; Δ∈=−3.1; $V_{th}$=2.30 V.

To the composition, compound (1-1-1-3-1) was added at a ratio of 0.4% by the weight.

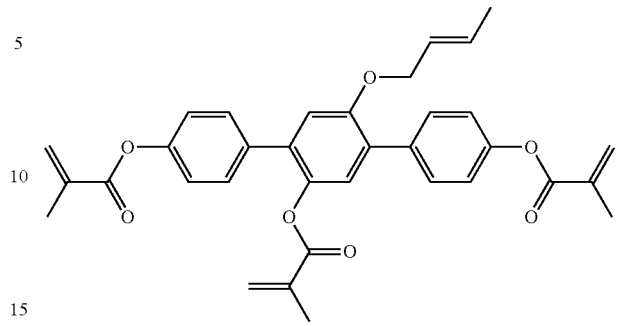

(1-1-1-3-1)

After polymerization was caused by irradiation with ultraviolet light, a response time thereof was measured: τ=3.8 ms.

Comparative Example 1

A response time of the composition before adding the compound (1-1-1-3-1) in Example 1 to the composition was measured: τ=5.6 ms.

The response time of the composition in Example 1 was 3.8 ms, and the response time of the composition in Comparative Example 1 was 5.6 ms. From the results, the PVA device in Example 1 was found to have a shorter response time than the response time of Comparative Example 1. Accordingly, the liquid crystal composition of the invention is concluded to have superior characteristics from a viewpoint of a liquid crystal display device having a polymer sustained alignment mode.

Example 2

| | | |
|---|---|---|
| 3-H1OB(2F,3F)-O2 | (2-3) | 8% |
| V2-BB(2F,3F)-O1 | (2-4) | 5% |
| V2-BB(2F,3F)-O2 | (2-4) | 9% |
| 1V2-BB(2F,3F)-O4 | (2-4) | 6% |
| V-HHB(2F,3F)-O2 | (2-6) | 10% |
| V-HHB(2F,3F)-O4 | (2-6) | 3% |
| 1V2-HHB(2F,3F)-O2 | (2-6) | 4% |
| 3-HH1OB(2F,3F)-O2 | (2-8) | 11% |
| 3-HH-V | (3-1) | 26% |
| 1-HH-2V1 | (3-1) | 5% |
| 5-HB-O2 | (3-2) | 4% |
| 3-HHB-O1 | (3-5) | 5% |
| V-HHB-1 | (3-5) | 4% |

A composition having negative dielectric anisotropy was prepared, and characteristics thereof were measured: NI=74.0° C.; $T_c$<−20° C.; Δn=0.101; Δ∈=−3.4; $V_{th}$=2.18 V.

To the composition, compound (1-1-1-2-1) was added at a ratio of 0.3% by weight and compound (4-2-3) was added at a ratio of 0.1% by weight.

(1-1-1-2-1)

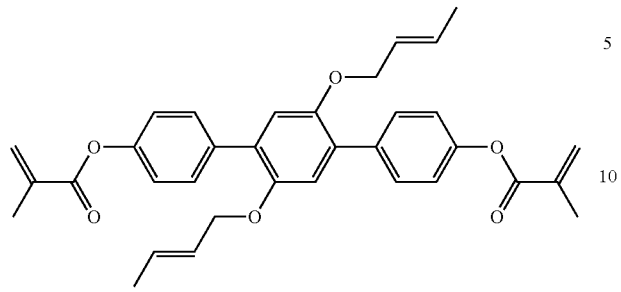

AC-VO-BB-OV-AC    (4-2-3)

After polymerization was caused by irradiation with ultraviolet light, a response time thereof was measured: τ=4.2 ms.

Example 3

| | | |
|---|---|---|
| 3-BB(2F,3F)-O2 | (2-4) | 9% |
| 2O-BB(2F,3F)-O2 | (2-4) | 3% |
| 2-HH1OB(2F,3F)-O2 | (2-8) | 10% |
| 3-HH1OB(2F,3F)-O2 | (2-8) | 20% |
| 2-BB(2F,3F)B-4 | (2-9) | 3% |
| 2-HH-3 | (3-1) | 19% |
| 3-HH-4 | (3-1) | 4% |
| 3-HH-V | (3-1) | 8% |
| V2-BB-1 | (3-3) | 3% |
| 1-BB-3 | (3-3) | 6% |
| V-HHB-3 | (3-5) | 5% |
| 3-HBB-2 | (3-6) | 4% |
| 5-B(F)BB-2 | (3-7) | 3% |
| 5-HBBH-3 | (3-11) | 3% |

A composition having negative dielectric anisotropy was prepared, and characteristics thereof were measured: NI=83.6° C.; $T_c$<−20° C.; Δn=0.108; Δ∈=−2.8; $V_{th}$=2.34 V.

To the composition, compound (1-1-1-5-1) was added at a ratio of 0.2% by weight, and compound (4-18-2) was added at a ratio of 0.2% by weight.

(1-1-1-5-1)

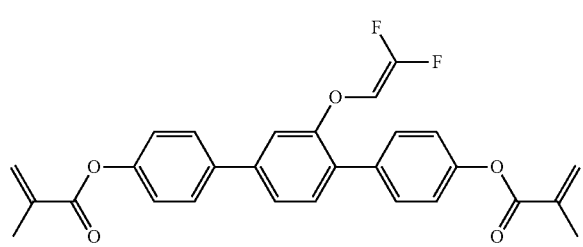

MAC-BB(F)B-AC    (4-18-2)

After polymerization was caused by irradiation with ultraviolet light, a response time thereof was measured: τ=3.7 ms.

Example 4

| | | |
|---|---|---|
| 3-BB(2F,3F)-O2 | (2-4) | 10% |
| 5-BB(2F,3F)-O4 | (2-4) | 3% |
| 2-HH1OB(2F,3F)-O2 | (2-8) | 10% |
| 3-HH1OB(2F,3F)-O2 | (2-8) | 22% |
| 2-HH-3 | (3-1) | 21% |
| 3-HH-V | (3-1) | 8% |
| 1-BB-3 | (3-3) | 8% |
| 1V2-BB-1 | (3-3) | 3% |
| V2-HHB-1 | (3-5) | 5% |
| 3-HBB-2 | (3-6) | 4% |
| 5-B(F)BB-3 | (3-7) | 3% |
| 1O1-HBBH-4 | (—) | 3% |

A composition having negative dielectric anisotropy was prepared, and characteristics thereof were measured: NI=78.6° C.; $T_c$<−20° C.; Δn=0.107; Δ∈=−2.6; $V_{th}$=2.39 V.

To the composition, compound (1-1-1-3-1) was added at a rate of 0.2% by weight, and compound (4-1-1) was added at a ratio of 0.2% by weight.

(1-1-1-3-1)

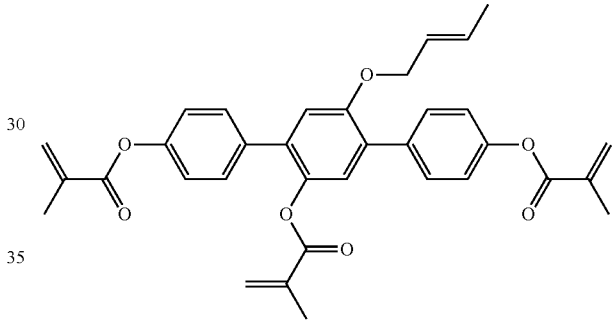

MAC-B(2F)B-MAC    (4-1-1)

After polymerization was caused by irradiation with ultraviolet light, a response time thereof was measured: τ=3.7 ms.

Example 5

| | | |
|---|---|---|
| V2-BB(2F,3F)-O2 | (2-4) | 12% |
| 1V2-BB(2F,3F)-O2 | (2-4) | 6% |
| 1V2-BB(2F,3F)-O4 | (2-4) | 3% |
| V-HHB(2F,3F)-O1 | (2-6) | 6% |
| V-HHB(2F,3F)-O2 | (2-6) | 12% |
| V-HHB(2F,3F)-O4 | (2-6) | 5% |
| 3-HDhB(2F,3F)-O2 | (2-11) | 5% |
| 3-dhBB(2F,3F)-O2 | (2-14) | 4% |
| 3-HH-V | (3-1) | 30% |
| 1-BB-3 | (3-3) | 6% |
| V-HHB-1 | (3-5) | 5% |
| 1-BB(F)B-2V | (3-8) | 3% |
| 3-HHEBH-4 | (3-9) | 3% |

A composition having negative dielectric anisotropy was prepared, and characteristics thereof were measured: NI=77.4° C.; $T_c$<−20° C.; Δn=0.112; Δ∈=−2.9; $V_{th}$=2.31 V.

To the composition, compound (1-1-1-3-1) was added at a ratio of 0.35% by weight, and compound (4-18-2) was added at a ratio of 0.05% by weight.

(1-1-1-3-1)

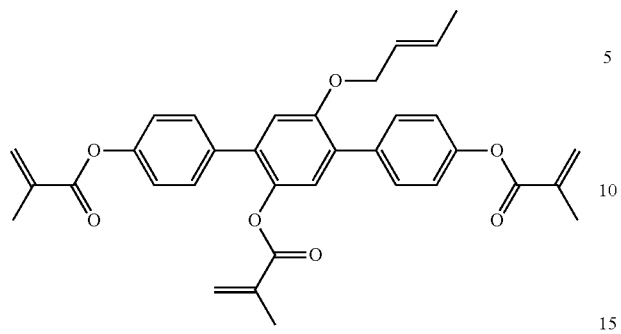

MAC-BB(F)B-AC (4-18-2)

After polymerization was caused by irradiation with ultraviolet light, a response time thereof was measured: τ=4.4 ms.

Example 6

| | | |
|---|---|---|
| V2-BB(2F,3F)-O2 | (2-4) | 12% |
| 1V2-BB(2F,3F)-O2 | (2-4) | 6% |
| 1V2-BB(2F,3F)-O4 | (2-4) | 3% |
| V-HHB(2F,3F)-O1 | (2-6) | 6% |
| V-HHB(2F,3F)-O2 | (2-6) | 7% |
| V-HHB(2F,3F)-O4 | (2-6) | 5% |
| 1V2-HHB(2F,3F)-O4 | (2-6) | 5% |
| 3-HDhB(2F,3F)-O2 | (2-11) | 5% |
| 3-dhBB(2F,3F)-O2 | (2-14) | 5% |
| 3-HH-V | (3-1) | 29% |
| V2-HB-1 | (3-2) | 6% |
| V-HHB-1 | (3-5) | 5% |
| 2-BB(F)B-5 | (3-8) | 3% |
| 5-HBB(F)B-3 | (3-13) | 3% |

A composition having negative dielectric anisotropy was prepared, and characteristics thereof were measured: NI=79.0° C.; $T_c$<−20° C.; Δn=0.112; Δ∈=−2.9; $V_{th}$=2.36 V.

To the composition, compound (1-1-1-12-1) was added at a ratio of 0.3% by weight, and compound (4-18-1) was added at a ratio of 0.1% by weight.

(1-1-1-12-1)

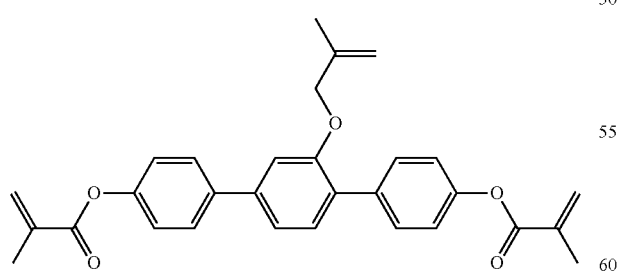

MAC-BB(F)B-OV-MAC (4-18-1)

After polymerization was caused by irradiation with ultraviolet light, a response time thereof was measured: τ=4.5 ms.

Example 7

| | | |
|---|---|---|
| 3-HB(2F,3F)-O2 | (2-1) | 3% |
| V2-BB(2F,3F)-O2 | (2-4) | 11% |
| 1V2-BB(2F,3F)-O2 | (2-4) | 6% |
| V2-HHB(2F,3F)-O2 | (2-6) | 5% |
| 3-HDhB(2F,3F)-O2 | (2-11) | 5% |
| 3-HBB(2F,3F)-O2 | (2-13) | 3% |
| V-HBB(2F,3F)-O2 | (2-13) | 6% |
| V2-HBB(2F,3F)-O2 | (2-13) | 6% |
| 3-dhBB(2F,3F)-O2 | (2-14) | 5% |
| 5-HH-O1 | (3-1) | 4% |
| 3-HH-V | (3-1) | 25% |
| 3-HH-VFF | (3-1) | 3% |
| 1-BB-3 | (3-3) | 6% |
| 3-HHEH-3 | (3-4) | 3% |
| V-HHB-1 | (3-5) | 6% |
| V2-HHB-1 | (3-5) | 3% |

A composition having negative dielectric anisotropy was prepared, and characteristics thereof were measured: NI=75.3° C.; $T_c$<−20° C.; Δn=0.113; Δ∈=−2.5; $V_{th}$=2.39 V.

To the composition, compound (1-1-1-8-1) was added at a ratio of 0.2% by weight, and compound (4-2-4) was added at a ratio of 0.1% by weight.

(1-1-1-8-1)

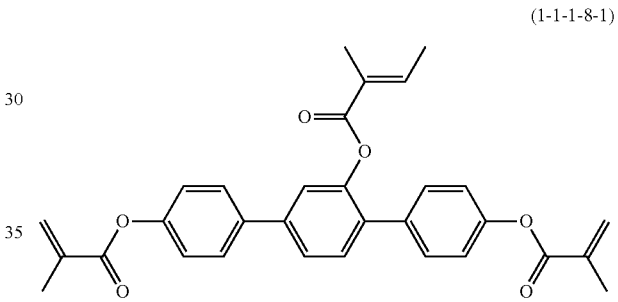

AC-VO-BB-MAC (4-2-4)

After polymerization was caused by irradiation with ultraviolet light, the response time thereof was measured: τ=4.4 ms.

Example 8

| | | |
|---|---|---|
| V2-BB(2F,3F)-O2 | (2-4) | 10% |
| 1V2-BB(2F,3F)-O2 | (2-4) | 4% |
| 1V2-BB(2F,3F)-O4 | (2-4) | 4% |
| V-HHB(2F,3F)-O1 | (2-6) | 6% |
| V-HHB(2F,3F)-O2 | (2-6) | 10% |
| V-HHB(2F,3F)-O4 | (2-6) | 5% |
| 3-DhH1OB(2F,3F)-O2 | (2-12) | 3% |
| 3-HHB(2F,3CL)-O2 | (2-16) | 3% |
| 5-HBB(2F,3CL)-O2 | (2-17) | 3% |
| 3-H1OCro(7F,8F)-5 | (2-18) | 3% |
| 3-HH1OCro(7F,8F)-5 | (2-19) | 3% |
| 3-HH-V | (3-1) | 29% |
| 1-BB-3 | (3-3) | 6% |
| V-HHB-1 | (3-5) | 7% |
| 3-HBB-2 | (3-6) | 4% |

A composition having negative dielectric anisotropy was prepared, and characteristics thereof were measured: NI=74.5° C.; $T_c$<−20° C.; Δn=0.105; Δ∈=−3.0; $V_{th}$=2.22 V.

To the composition, compound (1-1-1-3-1) was added at a ratio of 0.25% by weight, and compound (4-2-3) was added at a ratio of 0.05% by weight.

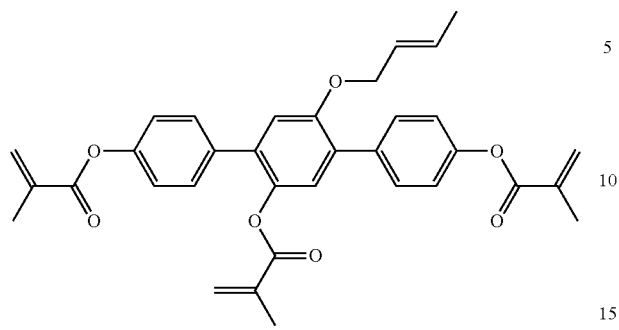

AC-VO-BB-OV-AC (4-2-3)

After polymerization was caused by irradiation with ultraviolet light, the response time thereof was measured: τ=4.8 ms.

Example 9

| | | |
|---|---|---|
| V2-HB(2F,3F)-O2 | (2-1) | 5% |
| 3-H2B(2F,3F)-O2 | (2-2) | 9% |
| V-HHB(2F,3F)-O2 | (2-6) | 12% |
| 2-HH1OB(2F,3F)-O2 | (2-8) | 7% |
| 3-HH1OB(2F,3F)-O2 | (2-8) | 12% |
| 3-HDhB(2F,3F)-O2 | (2-11) | 3% |
| 2-HH-3 | (3-1) | 27% |
| 3-HH-4 | (3-1) | 4% |
| 1-BB-3 | (3-3) | 9% |
| 3-HHB-1 | (3-5) | 3% |
| 3-B(F)BB-2 | (3-7) | 3% |
| 3-HB(F)HH-5 | (3-10) | 3% |
| 3-HB(F)BH-3 | (3-12) | 3% |

A composition having negative dielectric anisotropy was prepared, and characteristics thereof were measured: NI=79.9° C.; $T_c$<−20° C.; Δn=0.092; Δ∈=−2.9; $V_{th}$=2.32 V.

To the composition, compound (1-1-1-1-1) was added at a ratio of 0.2% by weight, and compound (4-23-1) was added at a ratio of 0.1% by weight.

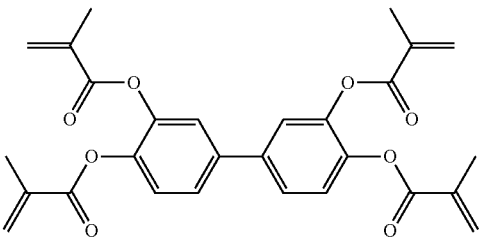

(4-23-1)

After polymerization was caused by irradiation with ultraviolet light, the response time thereof was measured: τ=3.9 ms.

Example 10

| | | |
|---|---|---|
| 1V2-HB(2F,3F)-O2 | (2-1) | 5% |
| 5-H2B(2F,3F)-O2 | (2-2) | 9% |
| 5-HHB(2F,3F)-O2 | (2-6) | 3% |
| V-HHB(2F,3F)-O2 | (2-6) | 6% |
| 2-HH1OB(2F,3F)-O2 | (2-8) | 7% |
| 3-HH1OB(2F,3F)-O2 | (2-8) | 12% |
| 2-BB(2F,3F)B-3 | (2-9) | 3% |
| 2-HHB(2F,3CL)-O2 | (2-16) | 3% |
| 4-HHB(2F,3CL)-O2 | (2-16) | 3% |
| 2-HH-3 | (3-1) | 22% |
| 3-HH-V | (3-1) | 8% |
| 1-BB-3 | (3-3) | 10% |
| 3-HHB-1 | (3-5) | 3% |
| 3-HB(F)HH-5 | (3-10) | 3% |
| 3-HB(F)BH-3 | (3-12) | 3% |

A composition having negative dielectric anisotropy was prepared, and characteristics thereof were measured: NI=80.5° C.; $T_c$<−20° C.; Δn=0.093; Δ∈=−2.9; $V_{th}$=2.32 V.

To the composition, compound (1-1-1-2-1) was added at a ratio of 0.1% by weight, and compound (1-1-1-3-1) was added at a ratio of 0.3% by weight.

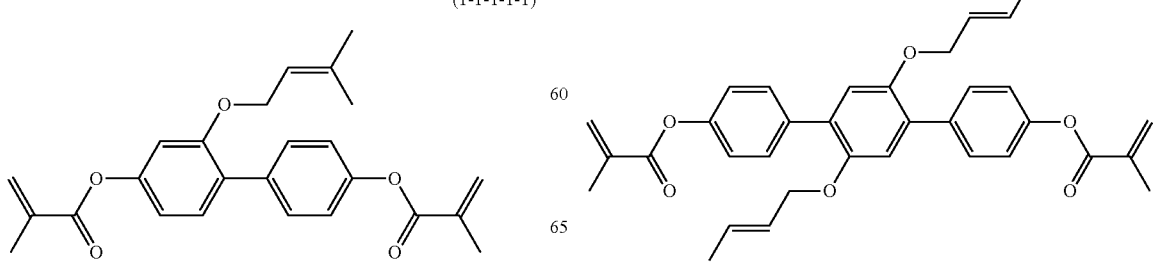

(1-1-1-3-1)

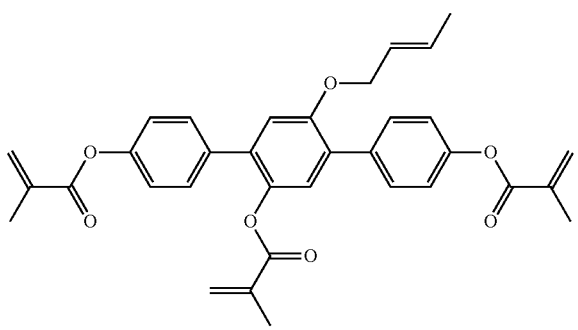

After polymerization was caused by irradiation with ultraviolet light, a response time thereof was measured: τ=4.3 ms.

Example 11

| | | |
|---|---|---|
| 3-HB(2F,3F)-O4 | (2-1) | 5% |
| V-HB(2F,3F)-O2 | (2-1) | 4% |
| V2-BB(2F,3F)-O2 | (2-4) | 7% |
| 1V2-BB(2F,3F)-O2 | (2-4) | 6% |
| 2O-B(2F,3F)B(2F,3F)-O6 | (2-5) | 3% |
| V-HHB(2F,3F)-O2 | (2-6) | 10% |
| 3-HH2B(2F,3F)-O2 | (2-7) | 3% |
| 3-HH1OB(2F,3F)-O2 | (2-8) | 10% |
| 2-BB(2F,3F)B-3 | (2-9) | 6% |
| 3-HH-V | (3-1) | 27% |
| 4-HH-V1 | (3-1) | 6% |
| 3-HH-2V1 | (3-1) | 3% |
| 3-HBB-2 | (3-6) | 7% |
| 5-HBB(F)B-2 | (3-13) | 3% |

A composition having negative dielectric anisotropy was prepared, and characteristics thereof were measured: NI=79.2° C.; $T_c$<−20° C.; Δn=0.112; Δ∈=−3.1; $V_{th}$=2.29V.

To the composition, compound (1-1-1-12-1) was added at a ratio of 0.4% by weight.

(1-1-1-12-1)

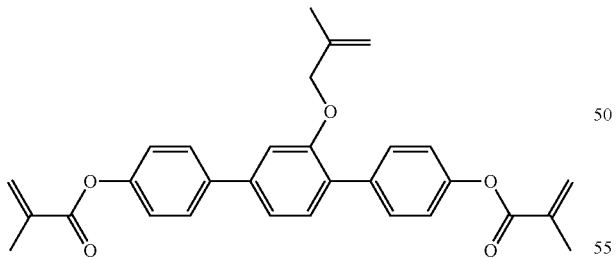

After polymerization was caused by irradiation with ultraviolet light, the response time thereof was measured: τ=4.1 ms.

Example 12

| | | |
|---|---|---|
| 3-HB(2F,3F)-O2 | (2-1) | 5% |
| V-HB(2F,3F)-O4 | (2-1) | 4% |
| 5-BB(2F,3F)-O2 | (2-4) | 6% |
| V2-BB(2F,3F)-O2 | (2-4) | 7% |
| 3-B(2F,3F)B(2F,3F)-O2 | (2-5) | 3% |
| V-HHB(2F,3F)-O2 | (2-6) | 10% |
| 3-HH1OB(2F,3F)-O2 | (2-8) | 10% |
| 2-BB(2F,3F)B-3 | (2-9) | 5% |
| 4-HBB(2F,3F)-O2 | (2-13) | 3% |
| 3-HBB(2F,3CL)-O2 | (2-17) | 3% |
| 3-HH-O1 | (3-1) | 3% |
| 3-HH-V | (3-1) | 24% |
| 3-HB-O2 | (3-2) | 3% |
| V-HHB-1 | (3-5) | 7% |
| 3-BB(F)B-5 | (3-8) | 3% |
| 5-HBB(F)B-2 | (3-13) | 4% |

A composition having negative dielectric anisotropy was prepared, and characteristics thereof were measured: NI=77.7° C.; $T_c$<−20° C.; Δn=0.117; Δ∈=−3.1; $V_{th}$=2.30V.

To the composition, compound (1-1-1-2-1) was added at a ratio of 0.35% by weight.

(1-1-1-2-1)

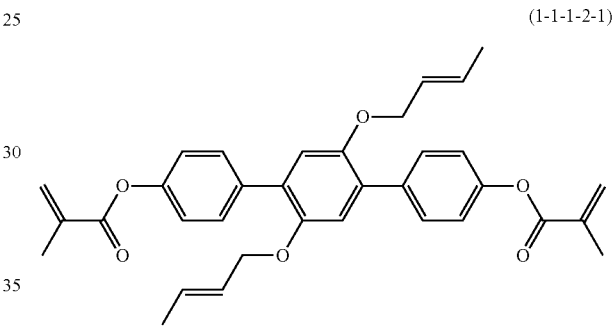

After polymerization was caused by irradiation with ultraviolet light, a response time thereof was measured: τ=4.8 ms.

Example 13

| | | |
|---|---|---|
| 3-BB(2F,3F)-O4 | (2-4) | 5% |
| V2-BB(2F,3F)-O2 | (2-4) | 12% |
| 1V2-BB(2F,3F)-O1 | (2-4) | 4% |
| 3-HHB(2F,3F)-O2 | (2-6) | 5% |
| V-HHB(2F,3F)-O1 | (2-6) | 6% |
| V-HHB(2F,3F)-O2 | (2-6) | 12% |
| 3-DhHB(2F,3F)-O2 | (2-10) | 5% |
| 3-HEB(2F,3F)B(2F,3F)-O2 | (2-15) | 5% |
| 3-HH-V | (3-1) | 23% |
| 4-HH-V | (3-1) | 3% |
| 5-HH-V | (3-1) | 6% |
| 7-HB-1 | (3-2) | 3% |
| V-HHB-1 | (3-5) | 5% |
| 3-HBB-2 | (3-6) | 3% |
| 2-BB(F)B-3 | (3-8) | 3% |

A composition having negative dielectric anisotropy was prepared, and characteristics thereof were measured: NI=76.3° C.; $T_c$<−20° C.; Δn=0.104; Δ∈=−3.0; $V_{th}$=2.21V.

To the composition, 0.1% by weight of compound (1-1-1-13) and 0.2% by weight of compound (4-18-1) were added.

(1-1-1-13)

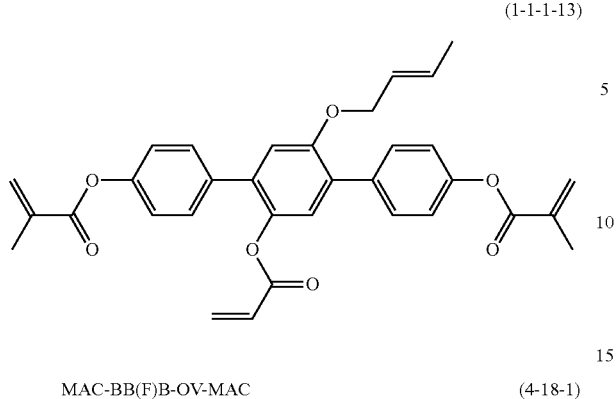

MAC-BB(F)B-OV-MAC (4-18-1)

After polymerization was caused by irradiation with ultraviolet light, the response time thereof was measured: τ=4.6 ms.

The compositions in Example 1 to Example 13 were found to have a shorter response time in comparison with the composition in Comparative Example 1. Accordingly, the liquid crystal composition according to the invention is concluded to have superb characteristics.

INDUSTRIAL APPLICABILITY

A liquid crystal composition of the invention satisfies at least one of characteristics such as a high maximum temperature, a low minimum temperature, a small viscosity, a suitable optical anisotropy, a large negative dielectric anisotropy, a large specific resistance, a high stability to ultraviolet light, a high stability to heat or the like, or has a suitable balance regarding at least two of the characteristics. A liquid crystal display device including the composition has characteristics such as a short response time, a large voltage holding ratio, a low threshold voltage, a large contrast ratio, a long service life and so forth, and thus can be used for a liquid crystal projector, a liquid crystal television and so forth.

What is claimed is:

1. A liquid crystal composition that has a negative dielectric anisotropy, and contains a polymerizable compound that is at least one compound selected from the group of compounds represented by formula (1):

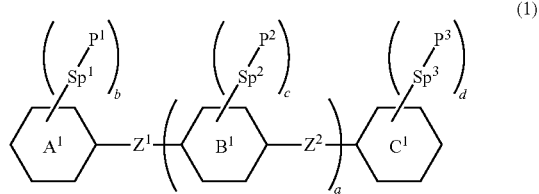

wherein, in formula (1), ring $A^1$ or ring $C^1$ is independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one of hydrogen may be replaced by halogen, alkyl having 1 to 12 carbons, or alkyl having 1 to 12 carbons in which at least one of hydrogen is replaced by halogen; ring $B^1$ is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one of hydrogen may be replaced by halogen, alkyl having 1 to 12 carbons, or alkyl having 1 to 12 carbons in which at least one of hydrogen may be replaced by halogen; $Z^1$ or $Z^2$ is independently a single bond or alkylene having 1 to 10 carbons, in the alkylene, at least one of —CH$_2$— may be replaced by —O—, —CO—, —COO— or —OCO—, at least one of —CH$_2$—CH$_2$— may be replaced by —CH=CH—, —C(CH$_3$)=CH—, —CH=C(CH$_3$)— or —C(CH$_3$)=C(CH$_3$)—, and in the groups, at least one of hydrogen may be replaced by fluorine or chlorine; at least one of $P^1$, $P^2$ and $P^3$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy, 2-methyl-2-butenyloxy or 2-methyl-2-propenyloxy; $Sp^1$, $Sp^2$ or $Sp^3$ is independently a single bond or alkylene having carbons 1-10, in the alkylene, at least one of —CH$_2$— may be replaced by —O—, —COO—, —OCO— or —OCOO—, at least one of —CH$_2$—CH$_2$— may be replaced by —CH=CH— or —C≡C—, and in the groups, at least one of hydrogen may be replaced by fluorine or chlorine; a is 0, 1 or 2; and b, c or d is independently an integer from 0 to 4, and a sum of b, c, and d is 2 or more.

2. The liquid crystal composition according to claim 1, wherein the polymerizable compound is at least one compound selected from the group of compounds represented by formula (1-1):

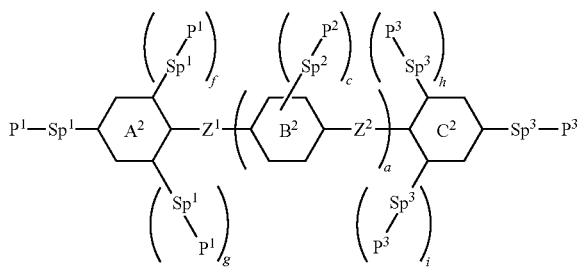

wherein, in formula (1-1), ring $A^2$, ring $B^2$ or ring $C^2$ is independently 1,4-cyclohexylene, 1,4-cyclohexenylene, 1,4-phenylene, naphthalene-1,2-diyl, naphthalene-1,4-diyl, naphthalene-1,5-diyl, naphthalene-1,7-diyl, naphthalene-1,8-diyl, naphthalene-2,3-diyl or naphthalene-2,6-diyl, and in the rings, at least one of hydrogen may be replaced by halogen, alkyl having 1 to 12 carbons, or alkyl having 1 to 12 carbons in which at least one of hydrogen is replaced by halogen; $Z^1$ or $Z^2$ is independently a single bond or alkylene having 1 to 10 carbons, in the alkylene, at least one of —CH$_2$— may be replaced by —O—, —CO—, —COO— or —OCO—, at least one of —CH$_2$—CH$_2$— may be replaced by —CH=CH—, —C(CH$_3$)=CH—, —CH=C(CH$_3$)— or —C(CH$_3$)=C(CH$_3$)—, and in the groups, at least one of hydrogen may be replaced by fluorine or chlorine; at least one of $P^1$, $P^2$ and $P^3$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy, 2-methyl-2-butenyloxy or 2-methyl-2-propenyloxy; $Sp^1$, $Sp^2$ or $Sp^3$ is independently a single bond or alkylene having 1 to 10 carbons, in the alkylene, at least one of —$CH_2$— may be replaced by —O—, —COO—, —OCO— or —OCOO—, at least one of —$CH_2$—$CH_2$— may be replaced by —CH=CH— or —C≡C—, and in the groups, at least one of hydrogen may be replaced by fluorine or chlorine; a is 0, 1 or 2; and c is an integer from 0 to 4, f, g, h and i each are 0 or 1, and a sum of c, f, g, h and i is 1 or more.

3. The liquid crystal composition according to claim 1, wherein the polymerizable compound is at least one compound selected from the group of compounds represented by formula (1-1-1):

(1-1-1)

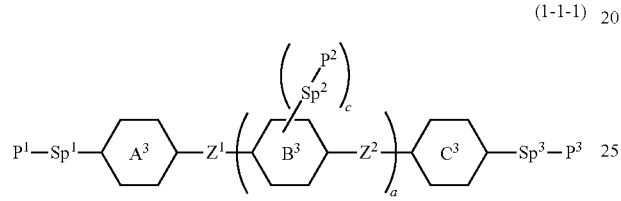

wherein, in formula (1-1-1), ring $A^3$, ring $B^3$ or ring $C^3$ is independently 1,4-phenylene in which at least one of hydrogen may be replaced by halogen, alkyl having 1 to 12 carbons, or alkyl having 1 to 12 carbons in which at least one of hydrogen is replaced by halogen; $Z^1$ or $Z^2$ is independently a single bond, —COO—, —CH=CH—, —CH=CH—COO—, —C($CH_3$)=CH—COO—, —CH=C($CH_3$)—COO—, —C($CH_3$)=C($CH_3$)—COO—, —COCH=CH—, —C($CH_3$)=C($CH_3$)—, —CH=CH—$CH_2$O—, —CH=CH—O$CH_2$— or —CO—; at least one of $P^1$, $P^2$ and $P^3$ is acryloyloxy or methacryloyloxy, and at least one remainder is 2-butenoyloxy, 2-methyl-2-butenoyloxy, 2-methylenebutanoyloxy, 2-methyl-1-propenyloxy, 2,2-difluorovinyloxy, 2-butenyloxy, 2-methyl-2-butenyloxy, or 2-methyl-2-propenyloxy; $Sp^1$, $Sp^2$ or $Sp^3$ is independently a single bond or alkylene having 1 to 10 carbons, in the alkylene, at least one of —$CH_2$— may be replaced by —O—, —COO—, —OCO— or —OCOO—, at least one of —$CH_2$—$CH_2$— may be replaced by —CH=CH— or —C≡C—, and in the groups, at least one of hydrogen may be replaced by fluorine or chlorine; a is 0, 1 or 2; and c is an integer from 0 to 4.

4. The liquid crystal composition according to claim 1, wherein the polymerizable compound is at least one compound selected from the group of compounds represented by formula (1-1-1-1) to formula (1-1-1-12):

(1-1-1-1)

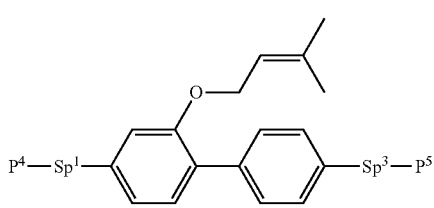

(1-1-1-2)

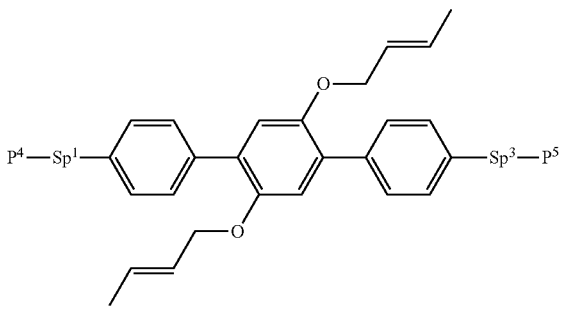

(1-1-1-3)

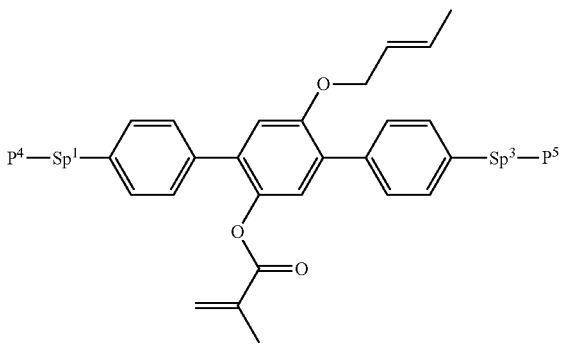

(1-1-1-4)

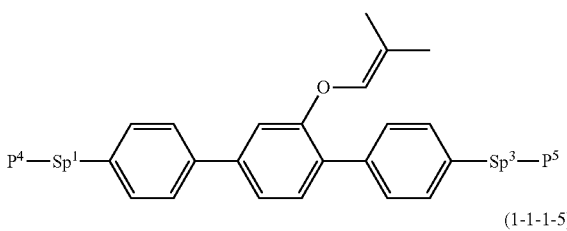

(1-1-1-5)

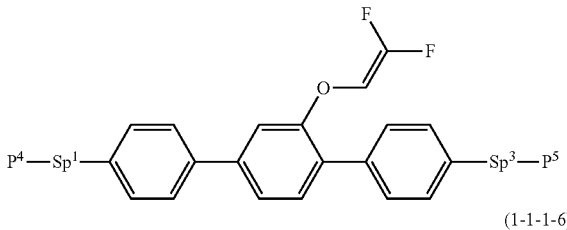

(1-1-1-6)

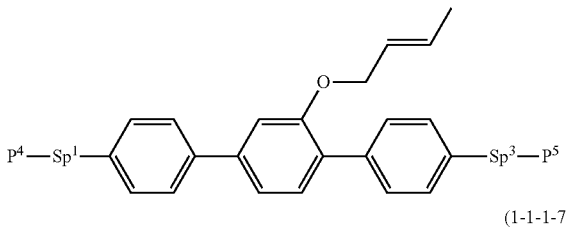

(1-1-1-7)

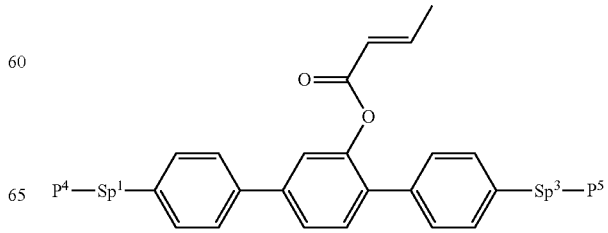

-continued

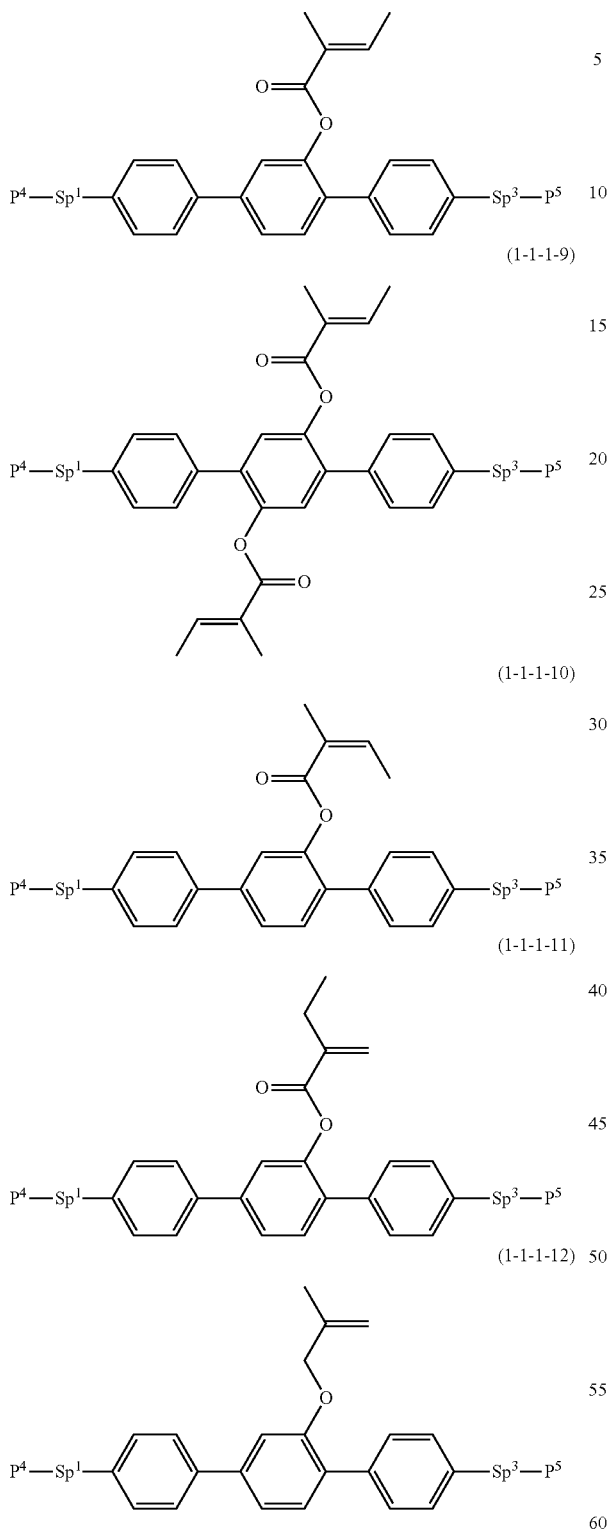

wherein, in formula (1-1-1-1) to formula (1-1-1-12), $P^4$ or $P^5$ is independently acryloyloxy or methacryloyloxy; and $Sp^1$ or $Sp^3$ is independently a single bond or alkylene having 1 to 10 carbons, in the alkylene, at least one of —$CH_2$— may be replaced by —O—, —COO—, —OCO— or —OCOO—, at least one of —$CH_2$—$CH_2$— may be replaced by —CH=CH— or —C≡C—, and in the groups, at least one of hydrogen may be replaced by fluorine or chlorine.

5. The liquid crystal composition according to claim 1, containing at least one compound selected from the group of compounds represented by formula (2) as a first component:

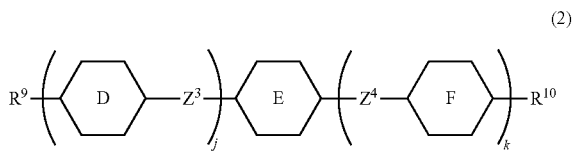

wherein, in formula (2), $R^9$ or $R^{10}$ is independently alkyl having 1 to 12 carbons, alkoxy having 1 to 12 carbons, alkenyl having 2 to 12 carbons or alkenyloxy having 2 to 12 carbons; ring D or ring F is independently 1,4-cyclohexylene, 1,4-phenylene, 1,4-phenylene in which at least one of hydrogen is replaced by fluorine or chlorine or tetrahydropyran-2,5-diyl; ring E is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl; $Z^3$ or $Z^4$ is independently a single bond, —$CH_2CH_2$—, —$CH_2O$—, —$OCH_2$—, —COO— or —OCO—; and j is 1, 2 or 3, k is 0 or 1, and a sum of j and k is 3 or less.

6. The liquid crystal composition according to claim 5, containing at least one compound selected from the group of compounds represented by formula (2-1) to formula (2-19) as the first component:

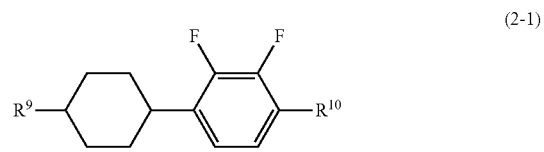

(2-1)

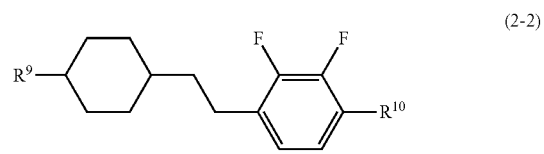

(2-2)

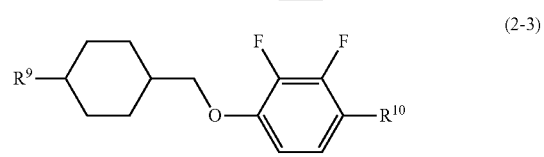

(2-3)

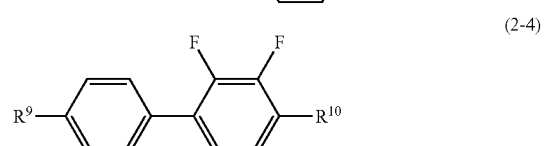

(2-4)

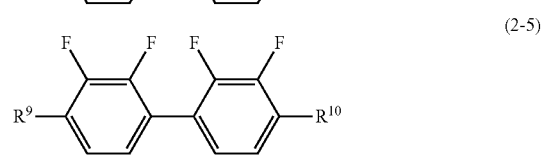

(2-5)

-continued (2-6) 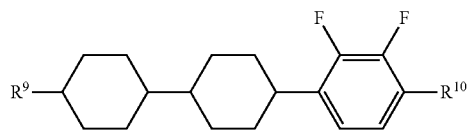

(2-7) 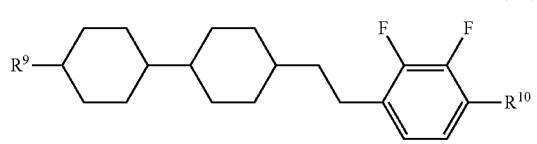

(2-8) 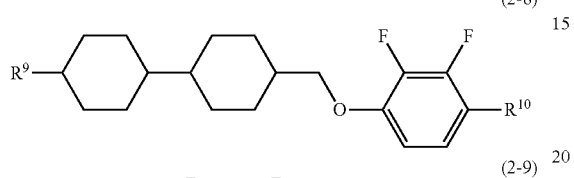

(2-9) 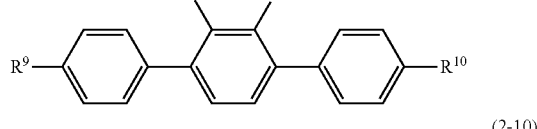

(2-10) 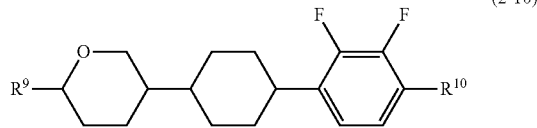

(2-11) 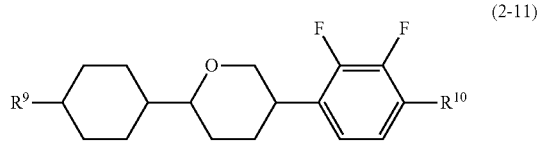

(2-12) 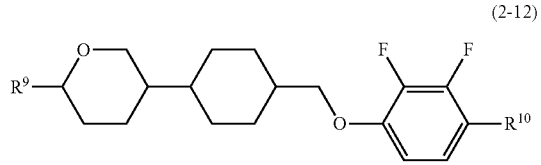

(2-13) 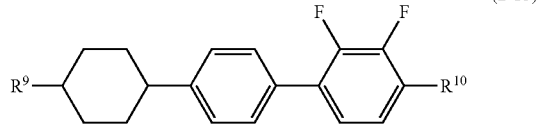

(2-14) 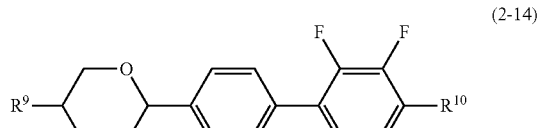

(2-15) 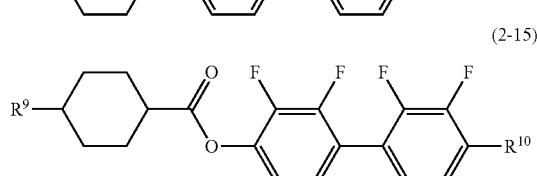

(2-16) 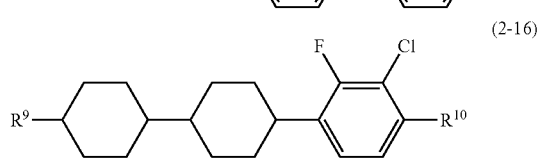

-continued (2-17) 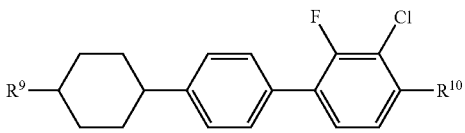

(2-18) 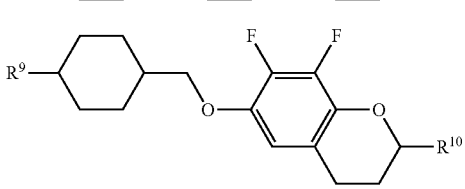

(2-19) 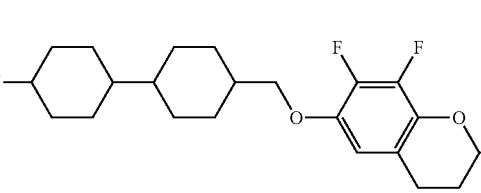

wherein, in formula (2-1) to formula (2-19), $R^9$ or $R^{10}$ is independently alkyl having 1 to 12 carbons, alkoxy having 1 to 12 carbons, alkenyl having 2 to 12 carbons or alkenyloxy having 2 to 12 carbons.

7. The liquid crystal composition according to claim 5, wherein a ratio of the first component is in the range of 10% by weight to 90% by weight based on the weight of the liquid crystal composition.

8. The liquid crystal composition according to claim 5, containing at least one compound selected from the group of compounds represented by formula (3) as a second component:

(3) 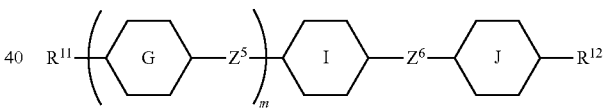

wherein, in formula (3), $R^{11}$ or $R^{12}$ is independently alkyl having 1 to 12 carbons, alkoxy having 1 to 12 carbons, alkenyl having 2 to 12 carbons, or alkenyl having 2 to 12 carbons in which at least one of hydrogen is replaced by fluorine; ring G, ring I or ring J is independently 1,4-cyclohexylene, 1,4-phenylene or 2-fluoro-1,4-phenylene; $Z^5$ or $Z^6$ is independently a single bond, —CH$_2$CH$_2$—, —CH$_2$O—, —OCH$_2$—, —COO— or —OCO—; and m is 0, 1 or 2.

9. The liquid crystal composition according to claim 8, containing at least one compound selected from the group of compounds represented by formula (3-1) to formula (3-13) as the second component:

(3-1) 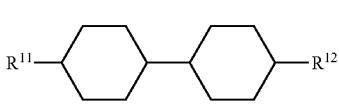

(3-2) 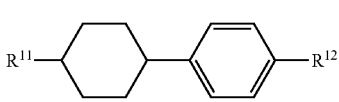

-continued

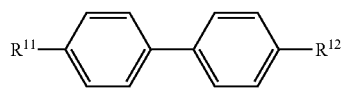
(3-3)

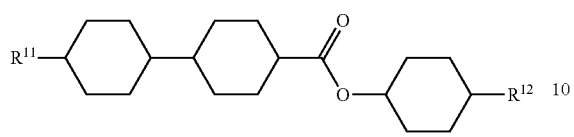
(3-4)

(3-5)

(3-6)

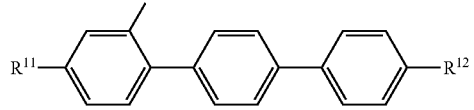
(3-7)

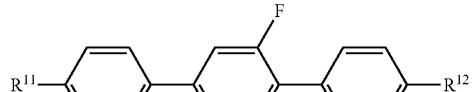
(3-8)

(3-9)

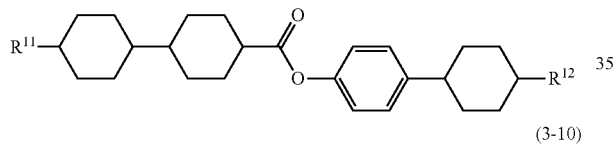
(3-10)

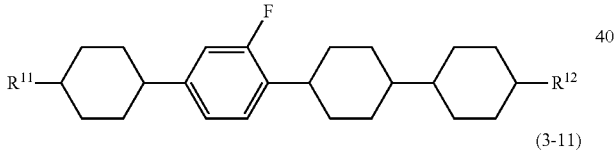
(3-11)

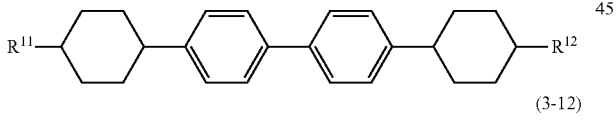
(3-12)

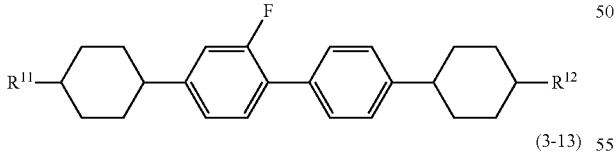
(3-13)

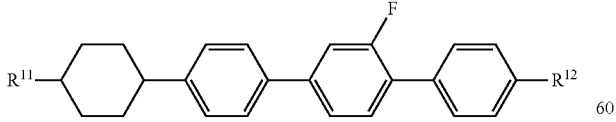

wherein, in formula (3-1) to formula (3-13), $R^{11}$ or $R^{12}$ is independently alkyl having 1 to 12 carbons, alkoxy having 1 to 12 carbons, alkenyl having 2 to 12 carbons, or alkenyl having 2 to 12 carbons in which at least one of hydrogen is replaced by fluorine.

10. The liquid crystal composition according to claim 8, wherein a ratio of the second component is in the range of 10% by weight to 90% by weight based on the weight of the liquid crystal composition.

11. The liquid crystal composition according to claim 6, further containing at least one polymerizable compound selected from the group of compounds represented by formula (4):

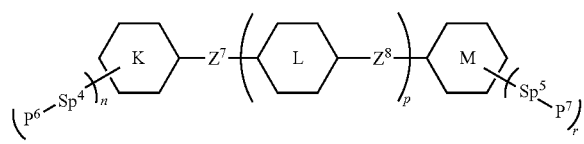
(4)

wherein, in formula (4), $P^6$ or $P^7$ is independently a polymerizable group selected from the group of groups represented by formula (P-4) or formula (P-5):

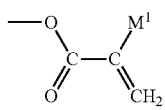
(P-4)

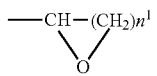
(P-5)

wherein, in formula (P-4), $M^1$ is hydrogen, fluorine, methyl or trifluoromethyl; and in formula (P-5), $n^1$ is 1, 2, 3 or 4; and in formula (4), $Sp^4$ or $Sp^5$ is independently a single bond or alkylene having 1 to 12 carbons, in the alkylene, at least one of —CH$_2$— may be replaced by —O—, —S—, —NH—, —CO—, —COO—, —OCO— or —OCOO—, at least one of —CH$_2$—CH$_2$— may be replaced by —CH═CH— or —C≡C—, and in the groups, at least one of hydrogen may be replaced by halogen or —C≡N; $Z^7$ is a single bond, —CH$_2$CH$_2$—, —CH$_2$O—, —OCH$_2$—, —COO—, —OCO—, —CO—CR$^{13}$═CR$^{14}$—, —CR$^{14}$═CR$^{13}$—CO—, —OCO—CR$^{13}$═CR$^{14}$—, —CR$^{14}$═CR$^{13}$—COO—, —CR$^{13}$═CR$^{14}$— or —C(═CR$^{13}$R$^{14}$)—, in which R$^{13}$ or R$^{14}$ is independently hydrogen, halogen, alkyl having 1 to 10 carbons, or alkyl having 1 to 10 carbons in which at least one of hydrogen is replaced by fluorine; $Z^8$ is a single bond, —CH$_2$CH$_2$—, —CH$_2$O—, —OCH$_2$—, —COO— or —OCO—; ring K or ring M is independently cyclohexyl, phenyl, 2-fluorophenyl, 3-fluorophenyl, 2,3-difluorophenyl, 2-methylphenyl, 3-methylphenyl, 2-(trifluoromethyl)phenyl, 3-(trifluoromethyl)phenyl or 2-naphthyl; ring L is 1,4-cyclohexylene, 1,4-phenylene, naphthalene-2,6-diyl, 2-fluoro-1,4-phenylene, 2,3-difluoro-1,4-phenylene, 2,5-difluoro-1,4-phenylene, 2-methyl-1,4-phenylene or 2-trifluoromethyl-1,4-phenylene; p is 0, 1 or 2; and n is 1, 2 or 3, r is 1, 2 or 3, and a sum of n and r is 4 or less.

12. The liquid crystal composition according to claim 11, further containing at least one polymerizable compound selected from the group of compounds represented by formula (4-1) to formula (4-26):

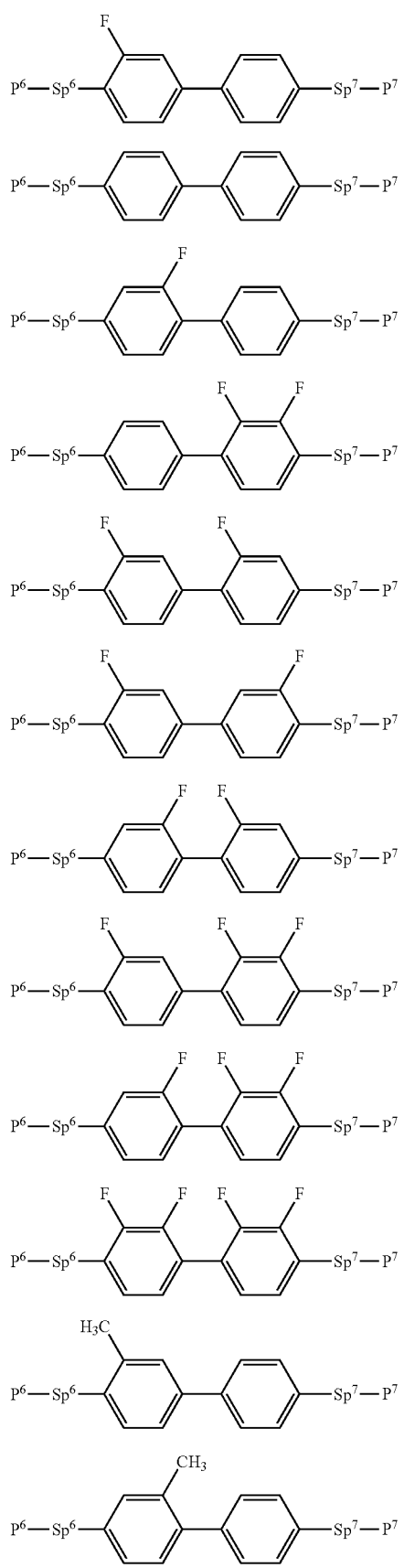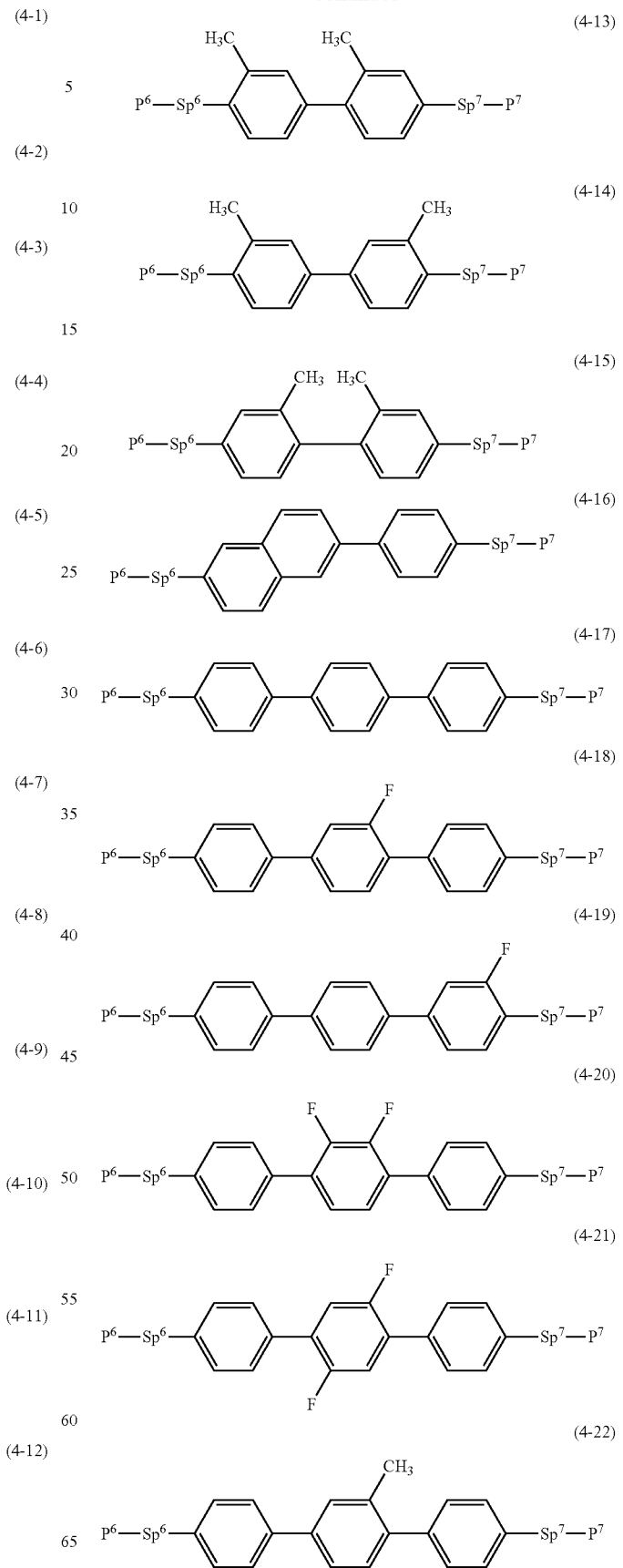

-continued (4-23)

(4-24)
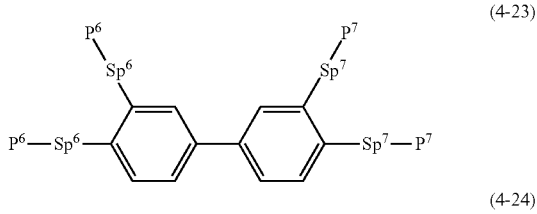

(4-25)
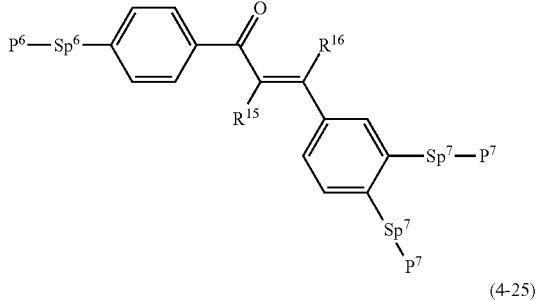

(4-26)
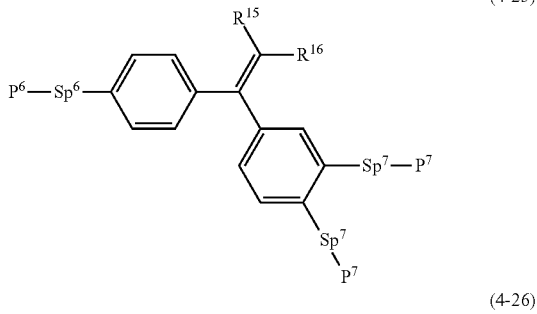

wherein, in formula (4-1) to formula (4-26), $P^6$ or $P^7$ is independently a polymerizable group represented by formula (P-4):

(P-4)

wherein, in formula (P-4), $M^1$ is hydrogen, fluorine, methyl or trifluoromethyl; and in formula (4-1) to formula (4-26), $Sp^6$ or $Sp^7$ is independently a single bond or alkylene having 1 to 12 carbons, in the alkylene, at least one of —$CH_2$— may be replaced by —O—, —COO—, —OCO— or —OCOO—, at least one of —$CH_2$—$CH_2$— may be replaced by —CH=CH— or —C≡C—, and in the groups, at least one of hydrogen may be replaced by fluorine or chlorine; and $R^{15}$ or $R^{16}$ is independently hydrogen, fluorine, chlorine, alkyl having 1 to 3 carbons, or alkyl having 1 to 3 carbons in which at least one of hydrogen is replaced by fluorine.

13. The liquid crystal composition according to claim 1, wherein a ratio of the polymerizable compound is in the range of 0.03% by weight to 10% by weight based on the weight of the liquid crystal composition.

14. A liquid crystal display device, including the liquid crystal composition according to claim 1.

15. The liquid crystal display device according to claim 14, wherein an operating mode in the liquid crystal display device includes an IPS mode, a VA mode, an FFS mode or an FPA mode, and a driving mode in the liquid crystal display device includes an active matrix mode.

16. A liquid crystal display device having a polymer sustained alignment mode, wherein the liquid crystal display device includes the liquid crystal composition according to claim 1, and a polymerizable compound in the liquid crystal composition is polymerized.

17. The liquid crystal composition according to claim 8, further containing at least one polymerizable compound selected from the group of compounds represented by formula (4):

(4)
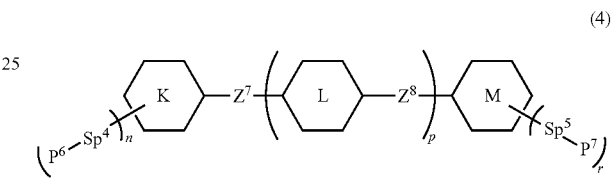

wherein, in formula (4), $P^6$ or $P^7$ is independently a polymerizable group selected from the group of groups represented by formula (P-4) or formula (P-5):

(P-4)

(P-5)

wherein, in formula (P-4), $M^1$ is hydrogen, fluorine, methyl or trifluoromethyl; and in formula (P-5), $n^1$ is 1, 2, 3 or 4; and in formula (4), $Sp^4$ or $Sp^5$ is independently a single bond or alkylene having 1 to 12 carbons, in the alkylene, at least one of —$CH_2$— may be replaced by —O—, —S—, —NH—, —CO—, —COO—, —OCO— or —OCOO—, at least one of —$CH_2$—$CH_2$— may be replaced by —CH=CH— or —C≡C—, and in the groups, at least one of hydrogen may be replaced by halogen or —C≡N; $Z^7$ is a single bond, —$CH_2CH_2$—, —$CH_2O$—, —$OCH_2$—, —COO—, —OCO—, —CO—$CR^{13}$=$CR^{14}$—, —$CR^{14}$=$CR^{13}$—CO—, —OCO—$CR^{13}$=$CR^{14}$—, —$CR^{14}$=$CR^{13}$—COO—, —$CR^{13}$=$CR^{14}$— or —C(=$CR^{13}R^{14}$)—, in which $R^{13}$ or $R^{14}$ is independently hydrogen, halogen, alkyl having 1 to 10 carbons, or alkyl having 1 to 10 carbons in which at least one of hydrogen is replaced by fluorine; $Z^8$ is a single bond, —$CH_2CH_2$—, —$CH_2O$—, —$OCH_2$—, —COO— or —OCO—; ring K or ring M is independently cyclohexyl, phenyl, 2-fluorophenyl, 3-fluorophenyl, 2,3-difluorophenyl, 2-methylphenyl, 3-methylphenyl, 2-(trifluoromethyl)phenyl, 3-(trifluoromethyl)phenyl or 2-naphthyl; ring L is 1,4-cyclohexylene, 1,4-phenylene, naphthalene-2,6-diyl, 2-fluoro-1,4-phenylene, 2,3-difluoro-1,4-phenylene, 2,5-difluoro-1,4-phenylene, 2-methyl-1,4-phenylene or 2-trifluoromethyl-1,4-phenylene; p is 0, 1 or 2; and n is 1, 2 or 3, r is 1, 2 or 3, and a sum of n and r is 4 or less.

* * * * *